United States Patent [19]

Reisfeld et al.

[11] Patent Number: 4,675,287

[45] Date of Patent: Jun. 23, 1987

[54] MONOCLONAL ANTIBODY DIRECTED TO HUMAN GANGLIOSIDE $GD_2$

[75] Inventors: Ralph A. Reisfeld, La Jolla; Gregor Schulz, San Diego, both of Calif.

[73] Assignee: Scripps Clinic and Research Foundation, La Jolla, Calif.

[21] Appl. No.: 634,687

[22] Filed: Jul. 26, 1984

[51] Int. Cl.[4] ............... G01N 33/53; G01N 33/544; C12P 21/00; C12N 15/00

[52] U.S. Cl. ...................... 435/7; 530/387; 530/808; 530/809; 424/85; 435/68; 435/172.2; 435/240; 435/948; 436/548; 436/813; 436/519; 436/528; 935/89; 935/95; 935/106; 935/107

[58] Field of Search ............ 424/85, 86, 87; 435/68, 435/172.2, 240, 241, 948, 43, 7, 29, 28, 171; 436/503, 513, 511, 518, 524, 528, 536, 804, 538, 540, 542, 548, 813, 821, 531, 533, 546, 800; 935/89, 95, 96, 100, 102, 103, 104, 107, 106, 108; 260/112 R; 530/387, 388

[56] References Cited

U.S. PATENT DOCUMENTS 4,172,124 10/1979 Koprowski et al. ............ 424/85
4,507,391 3/1985 Pukel et al. .................... 436/504

FOREIGN PATENT DOCUMENTS 0104014 3/1984 European Pat. Off.
2121417 12/1983 United Kingdom.

OTHER PUBLICATIONS

Schulz et al., Cancer Res 44 (12 Part 1), 5914–5920, Dec. 1984.
Irie et al., PNAS, vol. 79, 5666–5670, 1982.
Cahan et al., PNAS, vol. 79, 7629–7633, 1982.
Clifford et al., J Exp Med, vol. 155, 1133–1147, 1982.
Seeger et al., Advances in Neuroblastoma Research, pp. 443–458, 1985, Alan R. Liss, Inc.
Reynolds et al., "Autologous Marrow Transplantations, Proceedings 1st International Symposium", pp. 439–447, 1985, Diche, Spitzer & Zinden.
Reynolds et al., Transplantation Proceeding, vol. XVII, No. 1, pp. 434–436, 1985.

*Primary Examiner*—Christine M. Nucker
*Assistant Examiner*—Patricia L. DeSantis
*Attorney, Agent, or Firm*—Dressler, Goldsmith, Shore, Sutker & Milnamow, Ltd.

[57] ABSTRACT

A non-human, mammalian monoclonal receptor produced and secreted by a hybridoma having the ATCC accession number HB 8568 and methods of preparing and using same, as well as diagnostics utilizing the receptor are disclosed. The monoclonal receptor reacts with cells such as human neuroectodermal tumors having ganglioside $GD_2$ antigen expressed on their cellular membrane surfaces.

20 Claims, 9 Drawing Figures

MONOCLONAL ANTIBODY DIRECTED TO HUMAN GANGLIOSIDE GD$_2$

The Government of the United States of America has certain rights in this invention pursuant to Grant No. CA 28420 awarded by the National Institute of Health.

DESCRIPTION

1. Technical Field

The present invention relates to non-human, mammalian monoclonal receptors, and more particularly to non-human, mammalian monoclonal receptors that react with human tumor cells expressing ganglioside GD$_2$.

2. Background of the Invention

Neuroblastomas are highly malignant tumors occurring during infancy and early childhood. Except for Wilms' tumor, they are the most common retroperitoneal tumors in children. Neuroblastomas arise most commonly in the adrenal medulla, but they may also develop in other sympathetic ganglia within the thorax or abdomen. These tumors metastasize early with widespread involvement of lymph nodes, liver, bone, lung and marrow. The prognosis is often good when the tumor is diagnosed prior to obvious metastasis, but with metastasis, prognosis is poor despite the extensive use of radical surgery, deep X-ray therapy, and chemotherapeutic agents.

Several antigenic determinants have recently been detected on neuroblastoma cells with monoclonal antibodies (Mabs). See Seeger, *Ann. Intern. Med.*, 97, 873 (1982); Wikstrand et al., *Cancer Res.*, 42, 267 (1982); Wikstrand et al., *J. Neuroimmunlogy*, 3, 43 (1982); Eisenbarth et al., *Proc. Nat'l Acad. Sci. (USA)*, 76, 4913 (1979); Liao et al., *Eur. J. Immunol.*, 11, 450 (1981); Seeger et al., *Cancer Res.*, 4, 2714 (1981); Kennett et al., *Advances in Neuroblastoma Research*, p. 209, Raven Press, New York (Evans ed.) (1980); Seeger et al., *J. Immunol.*, 128, 983 (1982); Kemshead et al., *Pediatr. Res.*, 15, 1282 (1981).

A panel of such antibodies has been reported to be helpful in the differential diagnosis of neuroblastoma and lymphoblastic disorders, Kemshead et al., *Pediatr. Res.*, supra; Kemshead et al., *Lancet, i*, 12 (1983). In these same studies, antibodies were used either in immunoperoxidase assays with tumor tissue sections or in direct immunofluorescence assays to detect tumor cells in bone marrow aspirates. However, there have not been any reports describing the use of antibodies to neuroblastoma-associated antigens to detect elevated amounts of these antigens in the sera of patients and normal children.

The effective use of Mabs directed to any tumor-associated antigens as diagnostic reagents depends on the quantity, expression and chemical nature of the corresponding antigen. In this regard, Mabs directed to tumor-associated gangliosides have been useful in defining antigens associated with melanoma, neuroblastoma, colon carcinoma, and adenocarcinoma, Hakomori et al., *J. Natl. Cancer Inst.*, 71, 231 (1983). One of these antibodies was reported to detect a ganglioside antigen shed into the serum of patients with colon carcinomas, Koprowski et al., *Science*, 212, 53 (1981).

Some of the above neuroblastoma-associated antigens are present in fetal neural tissues whereas others are expressed by both fetal and adult neural tissues. Seeger, *Ann. Intern. Med.*, supra.

Most of the monoclonal antibodies utilized to detect the neuroblastoma-associated antigens are not restricted in their reactivity to neuroectodermal tumors like melanoma and glioma but also recognize common antigens on other malignancies such as a variety of sarcomas and leukemias, Seeger, *Ann. Intern. Med.*, supra. In addition, only some of the antigenic structures on neuroblastoma cells recognized by monoclonal antibodies have been partially characterized by immunochemical means. Thus, a monoclonal antibody designated Mab 390 was reported to react with an antigenic determinant of human Thy-1 that had a molecular weight of 25,000 daltons. Seeger et al., *J. Immunol.*, supra.

Another Mab, designated A$_2$B$_5$, was reported to recognize a GQ ganglioside on neurons, Eisenbarth et al., *Proc. Nat'l Acad. Sci. (USA)*, supra. A human monoclonal antibody produced in vitro by a lymphoblast cell line from a melanoma patient was also reported to react with a GD$_2$ ganglioside present on neuroectoderm-derived tumors, Cahan et al., *Proc. Nat'l Acad. Sci. (USA)*, 79, 7629 (1982).

From a biological point of view, gangliosides are of considerable interest since they have been implicated in a variety of cellular functions, including cell-cell adhesion and communication, as well as cell-substrate interactions, Hakomori et al., *J. Nat'l Cancer Inst.*, supra. Recent studies have emphasized the importance of gangliosides for tumor growth regulation by demonstrating differences in ganglioside composition among cells expressing various degrees of tumorgenicity, Itaya et al., *Proc. Nat'l Acad. Sci. (USA)*, 73, 1568 (1976). Consequently, the use of monoclonal antibodies directed to ganglioside determinants may aid in further delineating the role of gangliosides in these processes.

Most of the monoclonal antibodies directed against neuroblastoma-associated antigens that have been reported thus far, Wikstrand et al., *Cancer Res.*, supra; Wikstrand et al., *J. Neuroimmunology*, supra; Eisenbarth et al., *Proc Nat'l Acad. Sci. (USA)*, supra, recognize a common antigenic determinant on fetal tissues, especially fetal brain, as well as on adult brain and other neural tissues. In addition, cross-reactions of such antibodies have also been reported with normal kidney, fibroblasts, myoblasts, and thymocytes, Seeger et al., *Cancer Res.*, supra, and Seeger et al., *J. Immunol.*, supra, with islet cells, Eisenbarth et al., *Proc. Nat'l Acad. Sci. (USA)*, supra, and with spleen cells, Wikstrand et al., *Cancer Res.*, supra. Furthermore, some of the monoclonal antibodies reported in the literature are not only restricted in their reactivity to neuroectodermal tumors, such as neuroblastoma, melanoma and glioma, but also show binding to some forms of leukemia, osteogenic sarcoma, rhabdomyosarcoma, leiomyosarcoma and even to carcinomas of the lung and breast, Seeger, *Ann. Intern. Med.*, supra.

A monospecific human monoclonal antibody, (anti-OFA I-2), produced in vitro by a lymphoblast cell line that originated from a melanoma patient was reported to detect a GD$_2$ ganglioside on human melanoma, glioma and neuroblastoma cells, while reportedly not reacting with a variety of cell lines derived from carcinomas and from different lymphoid tumors, Cahan et al., *Proc. Nat'l Acad. Sci. (USA)*, supra, and Irie et al., *Proc. Nat'l Acad. Sci. (USA)*, 79, 5666 (1982). However, problems have arisen when such a human monoclonal antibody is used for immunoperoxidase assays of human tissues in that the anti-human secondary antibody required for such assays causes a large amount of nonspecific background reactivity.

Heterogeneity of neuroblastomas with regard to cell surface antigenic expression has been reported in Seeger, *Ann. Intern. Med.*, supra; Kemshead et al., *Pediatr. Res.*, supra; Kemshead et al., *Int. J. Cancer*, 27, 447 (1981); and, Kemshead et al., *Proc. Am. Assoc. Cancer Res.*, 2, 399 (1981). As discussed in these publications, Mab $A_2B_5$ failed to react with some human neuroblastoma lines tested, and quantitative differences in antigenic expression were observed between different cell cultures. Analysis of tumor cells in heavily infiltrated bone marrow aspirates indicated that only 70 percent of the samples reacted with $A_2B_5$, suggesting that the heterogeneity seen in the expression of antigen on cell lines is paralleled in fresh tumor material, Kemshead et al., *Int. J. Cancer*, supra.

SUMMARY OF THE INVENTION

The present invention contemplates a non-human, mammalian monoclonal receptor and methods of preparing and using same, as well as diagnostics utilizing the receptor. The monoclonal receptor is produced by a hybridoma formed by the fusion of a myeloma cell line and a lymphocyte that produces antibodies that react with ganglioside $GD_2$ such as splenocytes from a mammal immunized with human neuroectodermal tumor cells. The monoclonal receptor reacts with a ganglioside $GD_2$-containing immunogen.

In one aspect of the invention, a murine monoclonal receptor is produced by hybridoma ATCC HB 8568. This monoclonal receptor, designated Mab 126, was formed by fusion of cells from mouse myeloma line P3X63Ag8 and murine splenic cells from a mouse previously immunized with neuroblastoma cell line LAN-1. Monoclonal receptor Mab 126 reacts with fresh, frozen and formaldehyde-fixed cells that express the $GD_2$ ganglioside and does not react with fresh, frozen or formaldehyde-fixed cells that do not express the $GD_2$ ganglioside.

Mab 126 reacts with neuroblastoma cell lines, melanoma cell lines, glioma cell lines U138 MG and U87 MG, adenocarcinoma of adrenal cortex cell line SW13 and oat cell carcinoma cell line H69, all of which express ganglioside $GD_2$. The monoclonal receptor Mab 126 is substantially free from reaction with B-lymphoblastoid cell line LG2, B-lymphoblastoid cell line L14, T-cell leukemia cell line Molt-4, acute lymphoblastoic leukemia cell line HPB-All, Burkitt lymphoma cell line Daudi, Wilms' tumor cell line WIL-TU-1, Ewing sarcoma cell line SK-ES-2, osteogenic sarcoma cell line U-20S and rhabdomyosarcoma cell line A204, that do not express the ganglioside $GD_2$.

In addition, tne monoclonal receptor of the present invention reacts with frozen tumor tissues of neuroblastomas, melanomas, oat cell lung carcinomas, astrocytomas, glioblastomas multiforme and uterine leiomyomas. The present monoclonal receptor is substantially free from reaction with frozen tumor tissues of adenocarcinomas of the stomach, lung, breast, colon, prostate and ovary, fibrosarcomas, seminomas, non-Hodgkin's lymphomas, islet cell carcinomas and pleomorphic adenoma parotids. It also reacts with formaldehyde-fixed, tumor tissues from neuroblastomas and melanomas, but is substantially free from reaction with formaldehyde-fixed tissues from islet cell carcinomas, osteogenic sarcomas and embryonal rhabdomyosarcomas. The monoclonal receptor further reacts with frozen normal human tissues from the brain cortex, cerebellum, skin melanocytes and benign nevi, but is substantially free from reaction with frozen normal human tissues from the colon, spleen, pancreas, liver, lung, kidney and thyroid gland. It reacts with formaldehyde-fixed normal human tissues from the brain cortex, cerebellum, skin melanocytes and benign nevi, yet is substantially free from reaction with formaldehyde-fixed normal human tissues from the colon, spleen, pancreas, liver, lung and kidney.

The monoclonal receptor of the present invention is substantially free from reaction with frozen fetal tissues from the colon, spleen, adrenal gland, liver, lung and kidney, but reacts with formaldehyde-fixed fetal tissues from the brain cortex and cerebellum. It also reacts with ganglioside $GD_2$ antigen on the cellular surface of human neuroectodermal tumors and on the surface of frozen and formaldehyde-fixed human tissues.

In another aspect of the present invention, a diagnostic system for assaying for human neuroectodermal tumors is contemplated. The system includes, in at least one container, as an active ingredient, an effective amount of the above described non-human, mammalian monoclonal receptor. The system may also contain an indicating means.

In a further aspect of the present invention a hybridoma for the production of the above described monoclonal receptor, that reacts with neuroectodermal tumors having ganglioside $GD_2$ expressed thereon, is contemplated. The hybridoma is formed by fusion of cells from a myeloma line and non-human, mammalian splenic cells from a mammal previously immunized with a ganglioside $GD_2$ - containing immunogen.

In yet another aspect of the present invention, a method of preparing a hybridoma that produces the above described monoclonal receptor is contemplated. The method comprises (i) immunizing a mammal with neuroblastoma cell line LAN-1; (ii) removing the spleens from the mammal and making a suspension of the spleen cells; (iii) fusing the spleen cells with myeloma cells in the presence of a fusion promoter; (iv) diluting and culturing the fused cells in media that will not support the unfused myeloma cells to provide media having hybridoma cells and a supernatant; (v) evaluating the supernatants for the presence of receptor to neuroblastomas; and (vi) selecting and cloning the desired hybridoma that produces a monoclonal receptor to neuroblastomas.

In a still further aspect of the present invention, a method of preparing the above described monoclonal receptor is contemplated. The method comprises culturing the hybridoma ATCC HB 8568 in a suitable medium and recovering the receptor from the medium containing said hybridoma.

In yet another aspect of the present invention, a further method of preparing the above described monoclonal receptor is contemplated. The method comprises injecting into a mammal the hybridoma ATCC HB 8568 and recovering the receptor from the malignant ascites or serum of the mammal.

As it is highly cytotoxic to neuroblastoma cells in complement dependent cytotoxicity assays, the monoclonal receptor of the present invention is used for clearing tissue such as bone marrow of tumor cells in vitro in combination with complement. For another monoclonal receptor of this invention other than the particular monoclonal antibody disclosed herein, that does not fix complement, a complement activator such as cobra venom factor may be utilized. The tumor cells are contacted in vitro by admixture of the tumor cells and the monoclonal receptor. The complement or complement activator is supplied to the admixture from an external source.

In still another aspect of the present invention, a composition for killing neuroectodermal tumor cells having ganglioside $GD_2$ expressed thereon and a method for doing same are contemplated. The composition comprises an effective amount of the above described monoclonal receptor, complement and a physiologically tolerable diluent. The composition may further include an additional cytotoxic agent such as a drug. The method comprises contacting the tumor cells with the monoclonal receptor (a) in the presence of complement, or (b) as a carrier for a cytotoxic agent.

In a further aspect of the present invention, a remedial composition for treatment against neuroectodermal tumors having ganglioside $GD_2$ expressed thereon is contemplated. The remedial composition includes as an active ingredient, an effective amount of the above described monoclonal receptor dissolved or dispersed in a physiologically tolerable diluent.

In yet another aspect of the present invention, a composition for clearing tissue such as bone marrow of tumor cells in vitro is contemplated.

In a still further aspect of the present invention, a serological assay for the diagnosis and monitoring of neuroectodermal tumors having ganglioside $GD_2$ expressed thereon in mammalian serum is contemplated. The assay utilizes the above described monoclonal receptor as an active ingredient and an indicating means that, when introduced into a sample, binds selectively with the monoclonal receptor.

The present invention provides several benefits and advantages.

One benefit of the present invention is that the monoclonal receptor of the present invention is useful, inter alia, for the diagnosis of small round cell tumors in children as it distinguishes neuroblastomas from, for example, lymphoblastic lymphomas, leukemias, rhabdomyosarcomas and Ewing sarcomas. Another benefit is that the monoclonal receptor of the present invention is more restricted in its tissue distribution reactivity than are the previously reported monoclonal antibodies directed to neuroblastomas.

One of the advantages of the present invention is that the monoclonal receptor of the invention, when used for immunoperoxidase assays of human tissues does not cause non-specific background reactivity as do human Mabs directed to similar antigens.

Another advantage of the present invention is that, although considerable heterogeneity in antigen expression of neuroblastoma cell lines has been found when using the monoclonal receptor of the present invention in a fluorescence-activated cell sorter analysis, tne receptor, in contrast to other monoclonal antibodies previously reported, reacts with nearly one hundred percent of the population of positively staining cell lines.

Still another advantage of the invention is that the monoclonal receptor of the present invention strongly reacts in enzyme-linked immunobsorbent (ELISA) assays with substantially all neuroblastoma and melanoma cell lines, and avidly stains substantially all frozen and formaldehyde-fixed neuroblastoma and melanoma tissues.

Other advantages and benefits of the present invention will become readily apparent to those skilled in the art from the following description of the invention, the drawings and the appended claims.

BRIEF DESCRIPTION OF THE DRAWINGS

In drawings forming a portion of the disclosure of this invention:

FIG. 3 is divided into panels designated A, B and C wherein the LAN-2 cells were treated differently prior to being contacted with the receptors. In panel A, LAN-2 cells were dried on plates without any other treatment and then bound with the receptors. In panel B, the LAN-2 cells were dried on plates and thereafter heated at 100° C. for one hour followed by binding, while in panel C, the LAN-2 cells were pre-treated with 0.1 percent trypsin at room temperature, then plated, and thereafter bound.

DETAILED DESCRIPTION OF THE INVENTION

Figure 1:
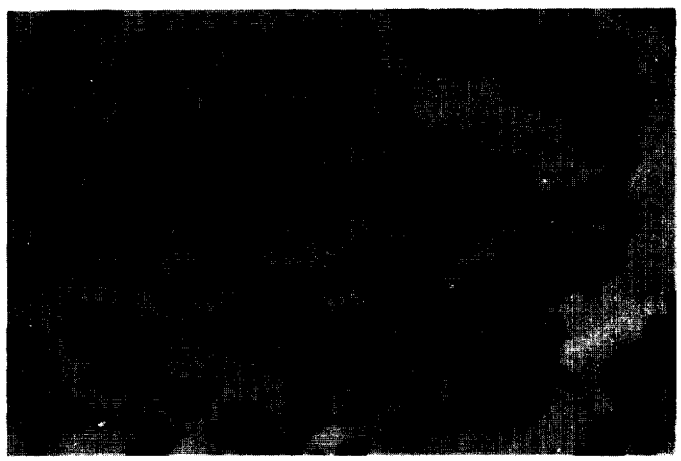
FIG. 1 is a copy of a photomicrograph showing a formaldehyde-fixed, paraffin-embedded neuroblastoma tissue, stained by the monoclonal receptor of the present invention using an immunoperoxidase technique described hereinafter in Section III.

The present invention is directed to a non-numan, mammalian monoclonal receptor and to methods of preparing and using same, as well as diagnostics utilizing the receptor. The monoclonal receptor reacts with human neuroectodermal tumors having ganglioside GD$_2$ antigen expressed thereon.

I. GENERAL DISCUSSION

The term "receptor" as used herein is meant to indicate a biologically active molecule that binds to a ligand. The receptor molecules of the present invention are intact or substantially intact antibodies or idiotype-containing polypeptide portions of antibodies. Biological activity of a receptor molecule is evidenced by the binding of the receptor to its antigenic ligand upon their admixture in an aqueous medium, at least at physiological pH values and ionic strengths. Preferably, the receptors also bind to the antigenic ligand within a pH value range of about 5 to about 9, and at ionic strengths such as that of distilled water to that of about one molar sodium chloride.

Idiotype-containing polypeptide portions (antibody combining sites) of antibodies are those portions of antibody molecules that include the idiotype and bind to the ligand, and include the Fab, and F(ab$_2$ portions of the antibodies. Fab and F(ab$_2$ portions of antibodies are well known in the art, and are prepared by the reaction of papain and pepsin, respectively, on substantially intact antibodies by methods that are well known. See for example, U.S. Pat. No. 4,342,566 to Theofilopolous and Dixon. Intact antibodies are preferred, and will be utilized as illustrative of the receptor molecules contemplated by this invention.

The receptors useful in the present invention are monoclonal receptors. A "monoclonal receptor" (Mab) is a receptor produced by clones of a single cell called a hybridoma that secretes but one kind of receptor molecule. The hybridoma cell is fused from an antibody-producing cell and a myeloma or other self-perpetuating cell line. Such receptors were first described by Kohler and Milstein, *Nature*, 256, 495–497 (1975), which description is incorporated herein by reference. Monoclonal receptors are typically obtained from hybridoma tissue cultures, the preferred method for obtaining the monoclonal receptor of the present invention, or, alternatively, from ascites fluid obtained from mammals into which the hybridoma tissue was introduced. Both methods are described hereinafter.

To form the hybridoma from which the monoclonal receptor is produced, a myeloma cell line is required to be fused with lymphocytes that produce antibodies that react with ganglioside GD$_2$, such as splenocytes from a mammal immunized with ganglioside GD$_2$ - containing immunogen, such as neuroectodermal tumor cells. The particular cell line used as an immunogen herein is neuroblastoma cell line LAN-1. However, any ganglioside GD$_2$ - containing immunogen is suitable for use in the present invention.

The lymphocytes that are employed may be derived from any mammal, such as primates, humans, rodents, e.g. mice, rats and rabbits, bovine, canine, ovine, or the like. As appropriate, the host may be sensitized by injection of the immunogen, in this instance cell line LAN-1, followed by a booster injection, and then isolation of the spleen.

It is preferred that the myeloma cell line be from the same species as the lymphocytes. Therefore, fused hybrids such as mouse-mouse hybrids [Shulman et al., *Nature*, 276, 269 (1978)] or rat-rat hybrids [Galfre et al., *Nature*, 277, 131 (1979)] are typically utilized. However, some rat-mouse hybrids have also been successfully used in forming hybridomas [Goding, "Production of Monoclonal Antibodies by Cell Fusion," in *Antibody as a Tool*, Marchalonis et al. eds., John Wiley & Sons Ltd., p. 273 (1982)]. Suitable myeloma lines for use in the present invention include MPC-11 (ATCC CRL 167), P3X63-Ag8.653 (ATCC CRL 1580), Sp2/0-Ag14 (ATCC CRL 1581), P3 X 63 Ag8U.1 (ATCC CRL 1597), Y3-Ag1.2.3. (deposited at Collection Nationale de Cultures de Microorganisms, Paris, France, number I-078) and P3X63Ag8 (ATCC TIB 9). Myeloma line P3X63Ag8 is preferred for use in the present invention.

The murine monoclonal receptor designated Mab 126 is a particularly preferred monoclonal receptor of the present invention. Mab 126 is an IgM monoclonal receptor, and recognizes a ganglioside antigen that is strongly expressed on all neuroblastoma and melanoma cell lines and tissues screened. It is believed that the ganglioside antigen recognized by Mab 126 is expressed on substantially all neuroblastoma and melanoma cells. Put differently, it is believed that Mab 126 reacts with ganglioside GD$_2$ and therefore it also reacts with substantially all cells that express qanglioside GD$_2$. Mab 126 is particularly reactive with neuroectodermal-derived tumor cells that express ganglioside GD$_2$.

In ELISA (enzyme-linked immunosorbant assay), the exemplary receptor of this invention failed to react with nearly all other lymphomas, sarcomas, and carcinoma cells lines with the exception of a cell line derived from an adenocarcinoma of the adrenal cortex and another cell line derived from a small cell carcinoma of tne lung. One out of three glioma cell lines screened was unreactive.

The screening of fresh frozen and formaldehyde-fixed normal and malignant tissues using tne immunoperoxidase technique again indicated that Mab 126 had its greatest reactivity with neuroblastoma and melanoma tumor tissues. Even this sensitive technique could not demonstrate strong binding of Mab 126 to glioma tumor tissues. Within normal tissues, there was only a faint positive reactivity with neural tissues and smooth muscle fibers supporting stroma.

Mab 126 differs distinctly from previously reported monoclonal antibodies directed against neuroblastoma-associated antigens since it is more restricted in its tissue-binding capabilities than are other monoclonal antibodies directed to neuroblastomas. Mab 126 also recognizes a common antigenic determinant on fetal tissues, especially fetal brain, as well as on adult brain and other neural tissues, as do most of the monoclonal antibodies previously reported.

However, cross-reactions of such previously reported antibodies with normal kidney, fibroblasts, myoblasts, thymocytes, islet cells and spleen cells are minimal with Mab 126. Furthermore, Mab 126 of this invention is substantially restricted in its reactivity to neuroectodermal tumors, such as neuroblastoma, melanoma and glioma, while some of the similarly derived monoclonal antibodies reported in the literature also show binding to some forms of leukemia, osteogenic sarcoma, rhabdomyosarcoma, leiomyosarcoma and even carcinomas of the lung and breast.

A monospecific human cell-derived antibody, (anti-OFA I-2), produced in vitro by a lymphoblast cell line originating from a melanoma patient has been reported to detect a $GD_2$ ganglioside on human melanoma, glioma and neuroblastoma cells. Similar to Mab 126, anti-OFA I-2 was reported not to bind to a variety of cell lines derived from carcinomas and from different lymphoid tumors, Cahan et al., *Proc. Nat'l Acad. Sci. (USA)*, supra; and, Irie et al; *Proc. Nat'l Acad. Sci. (USA)*, supra.

A non-human, mammalian monoclonal receptor such as Mab 126 has a particular advantage over a human cell-derived monoclonal antibody such as anti-OFA I-2 that recognizes a similar antigenic determinant when used for immunoperoxidase assays of human tissues. The advantage stems from the finding that the anti-human secondary antibody required for such assays causes a large amount of non-specific background reactivity. Use of Mab 126 does not provide such a background. Thus, the human Mab OFA I-2 has not been widely used for such assays.

Mab 126, in a fluorescence-activated cell sorter analysis, reacts with nearly 100 percent of the population of positively staining cell lines. On these cell lines, positive staining was evidenced by a brown color visible under a low power microscope. The brown color results from the reaction described in detail hereinafter. Furthermore, Mab 126 also strongly reacts in ELISA assays with all neuroblastoma and melanoma cell lines tested and avidly stains all frozen and formaldehyde fixed neuroblastoma and melanoma tissues. In view of these characteristics, Mab 126 is useful for the diagnosis of small round cell tumors in children, i.e., to distinguish neuroblastoma from lymphoblastic lymphoma, leukemia, rhabdomyosarcoma, and Ewing sarcoma. In this regard, it is well known that the differential diagnosis of these tumors has heretofore often been difficult, Reynolds et al., *Cancer*, 48, 2088 (1981); and, Raney et al., *J. Ped.*, 89, 433 (1976).

In contrast to many other tumor-associated antigens, such as those reported in Kemshead et al., *Lancet*, 1, 12 (1983), the ganglioside antigen recognized by Mab 126 is not denatured by the routinely used formaldehyde fixation. This feature adds to the usefulness of this receptor in clinical applicatons.

Another clinical use of Mab 126 is indicated by results of recent clinical investigations that suggest that patients with state IV neuroblastoma benefit from high dose chemotherapy and radiotherapy followed by rescue with autologous bone marrow, Hedley et al., *Exp. Haematol.*, 1, 360. Since Mab 126 is highly cytotoxic to neuroblastoma cells in complement dependent cytotoxicity assays, it is useful for clearing bone marrow of tumor cells in vitro in combination with complement. If receptors of this invention, other than Mab 126, that do not fix complement are used, a complement activator like cobra venom factor may be utilized in a bone marrow clearing method that may have a lower risk factor than use of antibody-toxin conjugates, Vogel et al., *Proc. Nat'l Acad. Sci. (USA)*, 78 7707 (1981). Briefly, this method includes the covalent binding of the cobra venom factor to the receptor, thus enabling the receptor to fix complement by activation of the alternative complement pathway. The linked venom-receptor conjugate may then be used as described in Section II B, hereinafter.

A further clinical use of Mab 126 is indicated by results that clearly demonstrate the presence of elevated levels of the ganglioside $GD_2$ in the sera of most patients with neuroblastoma compared to sera of normal children or patients with other pediatric tumors. These results suggest that the level of $GD_2$ antigen in the serum may be a useful marker for the diagnosis, monitoring and followup treatment of neuroblastoma patients.

A strong inhibition of binding of Mab 126 by preincubation with semi-purified gangliosides extracted from sera of neuroblastoma patients correlated with strong immunostaining of $GD_2$ in a TLC overlay assay. Because the recovery of the extraction procedure was nearly 100 percent, the log phase binding inhibition curve obtained with purified $GD_2$ may be used to calculate the actual amount of $GD_2$ in serum samples. The results suggest that 7 of 10 patients with Stage III and Stage IV melanoma also show elevated levels of $GD_2$ in their sera. This finding is in accord with reports that most melanoma tissues express a high amount of this antigen, Irie et al., *Proc. Natl. Acad. Sci. (USA)*, supra; Watanabe et al., *J. Exp. Med.*, 156, 1884 (1982).

Eighteen of twenty patients with other pediatric tumors did not present elevated $GD_2$ levels. However, it is of some interest that one of three serum samples of patients with Wilms'tumor and another sample from one of two osteogenic sarcoma patients showed elevated amounts of $GD_2$. This was particularly surprising since cell lines as well as tissues of these histologic types of tumors failed to react with Mab 126.

Reports have suggested that Mabs may be useful in the detection of tumor-associated antigens in serum of patients with melanoma and colon carcinoma, Koprowski et al., *Science*, supra; Gupta et al., *J. Natl. Cancer Inst.*, 72, 75 (1984); Morgan et al., *Cancer*, 48, 2088 (1981). However, the results discussed herein concern developing effective methods for diagnosis of neuroblastoma in tissue and serum samples, mainly because the differential diagnosis of this tumor is often more difficult than that for glioma or melanoma. In fact, neuroblastomas are at times quite difficult to distinguish histopathologically from other round cell tumors in children, i.e., lymphoblastic lymphoma, leukemia, rhabdomyosarcoma, or Ewing's sarcoma, Kemshead et al., *Lancet*, supra; Reynolds et al., *Cancer*, supra; Raney et al., *J. Ped.*, supra. Consequently, a serum assay for neuroblastoma requiring only small volumes of blood is indeed most advantageous, especially since other diagnostic tests for neuroblastoma; i.e., assays for catecholamines and their metabolites require a special diet and the collection of 24 hour urine volumes, both of which are difficult to maintain with small children. In addition, these metabolic tests are sometimes negative because some neuroblastomas are cholinergic or inactive rather than adrenergic, Seeger et al., *Ann. Intern. Med.*, supra.

In addition to the diagnostic utility of Mab 126, additional results indicate that it is useful for prognostic purposes. In this regard, the serum $GD_2$ level of a patient was followed serially, and Mab 126 was used to show a remarkable correlation of the serum $GD_2$ level with the progression of disease.

It has been reported that an antibody from a melanoma patient recognized an autoantigenic ganglioside related to $GD_2$, Watanabe et al., *J. Exp. Med.*, supra. The antibody proved to react relatively specifically with neuroectodermal-derived tumors when tested by immune adherence assays. However, the study employing the human antibody failed to apply the more discriminating immunoperoxidase technique for staining of frozen and paraffin-embedded normal and tumor tissues that also provides more useful information for clinical purposes, since it detects even small tumor infiltrates and metastases into normal organs. In addition, there is thus far no published report providing a complete description of the tissue distribution of the $GD_2$ antigen in normal tissues.

The data from several studies, discussed hereinafter, that were performed to assess the chemical nature of the antigen recognized by Mab 126 indicate that the antigen is a ganglioside. Thus, the antigenic determinant recognized by Mab 126 was not destroyed by heat (100° C., 1 hr.) or trypsin treatment, suggesting that it is not a protein. Furthermore, antibody binding to neuroblastoma target cells was inhibited by preincubation of antibody supernatant with glycolipids or purified gangliosides isolated from this tumor. Finally, binding inhibition was eliminated when those extracts were pretreated with sialidase. In this regard, the results discussed below indicate that the antigen is, in fact, the disialoganglioside $GD_2$ (disialosyl-N-triglycosyl ceramide).

Specifically, gangliosides separated by one-dimensional thin layer chromatography when reacted with Mab 126 showed immunostaining of a single ganglioside component that comigrated with purified $GD_2$. In addition, purified $GD_2$ specifically inhibited Mab 126 binding to neuroblastoma or melanoma cell targets. It is believed that the tumor cell lines and tissues that did not react with Mab 126 in studies whose results are shown in Tables I and II hereinafter, do not contain sufficient amounts of the ganglioside $GD_2$ expressed on their cell membrane surfaces to be detected by these methods.

In the results discussed below, ganglioside $GD_2$ was obtained from human neuroblastoma LAN-1 cell lines. However, LAN-1 cell lines are but one source of a ganglioside $GD_2$-containing immunogen. Ganglioside $GD_2$ is present across substantially all non-human, mammalian species and may be obtained from substantially any source.

The results discussed below were also obtained using the Mab 126 embodiment of this invention. It is to be understood, however, that the results discussed hereinbelow are illustrative of embodiments utilizing Mab 126 and the present invention is not intended to be so limited.

II. RESULTS

A. Antigen Reactivity and Recognition Assays

1. ELISA Reactivity of Monoclonal Antibody 126 with Different Tumor Cell Lines

The ability of Mab 126 to bind to various cells was screened using thirty different cell lines. Binding of Mab 126 to those cells was determined by a standard enzyme-linked immunoabsorbent assay (ELISA technique) discussed in detail hereinafter in Section III. The binding reaction pattern obtained is shown in Table I below:

TABLE I

Reactivity of Mab 126 with Different Cell Lines in ELISA Assay

| Cell line | Tumor type | Reactivity | Cell line | Tumor type | Reactivity |
|---|---|---|---|---|---|
| | Neuroblastomas | | | | |
| LAN-1 | | +++[1] | LG2 | B-lymphoblastoid | − |
| LAN-2 | | +++ | L14 | cells | |
| LAN-5 | | +++ | Molt-4 | T-cell leukemia | − |
| SK-N-SH | | +++ | HPB-All | acute lymphoblastoic leukemia | − |
| | | | Daudi | Burkitt Lymphoma | − |
| | Melanomas | | T 291 | Adeno Carcinoma (lung) | − |
| M14 | | +++ | CALU 6 | Anaplastic Carcinoma | − |
| M21 | | +++ | SCI-1185 | Squamous Carcinoma (skin) | − |
| FM3 | | +++ | UCLAP3 | Adeno Carcinoma (lung) | − |
| FM8 | | +++ | SW13 | Adeno Carcinoma (adrenal cortex) | ++[3] |
| FL2 | | +++ | Panc 1 | Pancreatic Carcinoma | − |
| Foss | | +++ | H69 | Oat cell Carcinoma | ++ |
| Mueller | | +++ | | | |
| | Gliomas | | WIL-TU-1 | Wilms Tumor | |
| U373 MG | | −[2] | SK-ES-2 | Ewing sarcoma | − |
| U138 MG | | +++ | U-20S | Osteogenic sarcoma | − |
| U87 MG | | +++ | A204 | Rhabdomyosarcoma | − |

[1] "+++" indicates binding reactivity is more than four times higher than non-immune Ig from the myeloma partner, Ig × 63.
[2] "−" indicates that no binding reactivity was observed.
[3] "++" indicates binding reactivity is 3–4 times higher than Ig × 63.

As can be seen in Table I, all seven melanoma cell lines as well as all four neuroblastoma cell lines of this study exibited strongly positive binding by (reaction with) Mab 126. The glioma cell line U373 MG was negative, whereas two other glioblastoma cell lines were strongly positive. Two of the seven carcinoma cell lines that showed binding were of neuroectodermal origin; i.e., the oat cell carcinoma cell line H69 and cell line SW13 derived from an adenocarcinoma of adrenal cortex. Mab 126 did not bind to two B-lymphoblastoid and two T-cell leukemia cell lines, nor to cell lines derived from a Wilms'tumor, Ewing sarcoma, osteogenic sarcoma, and rhabdomyosarcoma. In addition, the antibody failed to react with leukemic cells isolated from peripheral blood from 6 patients with different kinds of leukemia. These data indicate that the antigen recognized and bound by Mab 126 is preferentially expressed on cell lines derived from neuroectodermal tumors with tne exception of the glioma cell line U373 MG, that is believed not to express ganglioside $GD_2$ or if that ganglioside is expressed, its binding by a receptor is significantly hindered.

2. Reactivity of Mab 126 with Different Frozen or Formalin-Fixed Normal and Malignant Tissues The ability of Mab 126 to bind to a relatively large number of frozen or formalin-fixed (formaldehyde-fixed) normal and malignant tissues was also screened. Binding was assayed by an immunoperoxidase technique discussed hereinafter in Section III.

All seven neuroblastoma including two metastases in testis and four melanoma tissues were found to show strongly positive binding. In an oat cell tumor tissue, only 50 percent of the cells were stained, while a glioma tissue showed only a very faint staining. A variety of tumor tissues from patients with fibrosarcoma, non-Hodgkin's lymphoma, osteogenic sarcoma, rhabdomyosarcoma, Wilms'tumor and different types of carcinoma were not bound by the receptor.

Among normal tissues, there was very slight reactivity with cerebral and cerebellar gray matter, skin melanoyctes and nevi. Mab 126 also reacted faintly with smooth muscle of blood vessels, supporting stroma and a benign leiomyoma. Most of the fetal tissues screened were also not bound by Mab 126 with the exception of those tissues from the brain and cerebellum. The results of these binding studies are summarized in Table II below:

TABLE II

Tissue Reactivity of Monoclonal Antibody 126 by Immunoperoxidase Assays

| Tumor Tissues | Frozen | Fixed | Normal Tissues | Frozen | Fixed |
|---|---|---|---|---|---|
| Neuroblastoma | +++[1] | +++ | Colon | —**[7] | — |
| Melanoma | +++ | +++ | Spleen | — | — |
| Oat cell carcinoma (lung) | +[2] | ND[3] | Pancreas | — | — |
|  |  |  | Liver | —** | — |
|  |  |  | Lung | — | — |
| Adenocarcinomas |  |  | Brain cortex | ± | + |
|  |  |  | Cerebellum | ± | + |
| Stomach | —*[4] | ND | Kidney | — | — |
| Lung | —* | ND | Thyroid | —** | ND |
| Breast | —* | ND | Skin melanocytes | + | + |
| Colon | —* | ND |  |  |  |
| Prostate | —* | ND | Benign nevus | +* | + |
| Ovary | —* | ND | Fetal Tissues |  |  |
| Fibroscarcom | —[5] | ND | Colon | —** | ND |
| Seminoma | — | ND | Spleen | —** | ND |
| Non-Hodgkin's lymphoma | — | ND | Adrenal | —** | ND |
|  |  |  | Liver | —** | ND |
| Islet cell carcinoma | — | — | Lung | —** | ND |
|  |  |  | Brain cortex | ND | + |
| Astrocytoma | ±[6] | ND | Cerebellum | ND | + |
| Glioblastoma Multiforme | ± | ND | Kidney | —** | ND |
| Leiomyoma (uterus) | + | ND |  |  |  |
| Pleomorphic adenoma parotid | — | ND |  |  |  |
| Osteogenic sarcoma | ND | — |  |  |  |
| Embryonal rhabdomyosarcoma | ND | — |  |  |  |
| Wilms' tumor | ND | — |  |  |  |

[1] "+++" indicates strong binding reactivity.
[2] "+" indicates binding reactivity.
[3] "ND" indicates binding reactivity not determined.
[4] *indicates that the supporting stroma of smooth muscle adjacent to tumor cells showed slight binding reactivity.
[5] "—" indicates no binding reactivity.
[6] "±" indicates slight binding reactivity.
[7] *indicates smooth muscle around blood vessels showed slight binding reactivity.

Figure 2:
FIG. 2 is a copy of a photomicrograph showing staining of a similar tissue sample area as in FIG. 1 using a non-immune immunoglobulin (Ig) P3X63Ag8 supernatant, hereinafter sometimes referred to as X63, instead of the monoclonal receptor of the present invention.

FIGS. 1 and 2 illustrate typical staining observed when Mab 126 was admixed with and bound to a formaldehyde-fixed, paraffin-embedded neuroblastoma tissue as compared to that observed when the same tissue was similarly treated witn a non-immune immunoglobulin (Ig); i.e., the X63 supernatant. These figures clearly depict the very strong staining obtained by Mab 126 with all tumor cells of the tissue section shown.

It is of interest that at the time the above binding study was carried out, each of the particular tumors had been fixed and embedded for more than six months. The strongly positive staining obtained therefore indicates that the antigen recognized by Mab 126 was not denatured by either formaldehyde or by prolonged storage.

3. Identity of Antigen Recognized By Mab 126

Since Mab 126 did not immunoprecipitate a protein, it was suspected that its corresponding antigen may be a carbohydrate determinant on a glycolipid. In order to characterize the nature of the antigen recognized by Mab 126, the heat stability of the antigen was examined. For this purpose, an ELISA plate containing dried LAN-2 cells was cut into two equal portions, each having 48 wells. One portion was incubated for one hour at a temperature of 100° C. Thereafter, ELISA assays for the binding of Mab 126 to the LAN-2 cells were performed on both portions of the plate using the technique described hereinafter.

Figure 3:
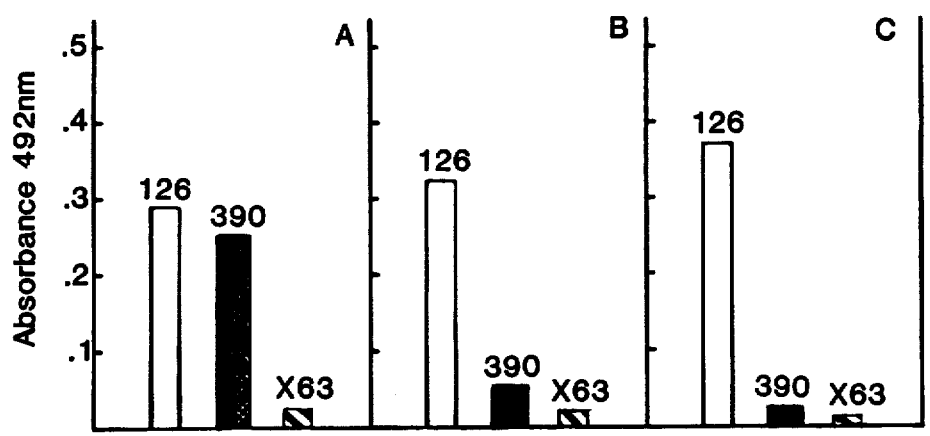
FIG. 3 is a graph illustrating the binding to LAN-2 neuroblastoma cells in an ELISA assay of three different monoclonal receptors denominated Mab 126 (of this invention), 390 and X63, respectively.

As shown in FIG. 3, the binding of Mab 126 to heated LAN-2 cells (panel A) was at least equal to if not greater than that observed with normal LAN-2 cells (panel B), indicating that the antigenic determinant is heat stable. In contrast, the binding of Mab 390 to its corresponding glycoprotein Thy-1 antigen, was markedly decreased after this heat treatment (panels A and B).

It was also demonstrated that preincubation of LAN-2 cells previously treated with 0.1 percent trypsin (10 minutes, 23° C.) did not inhibit the binding efficiency of Mab 126 when compared to that of untreated cells (panel C). However, the binding capacity of Mab 390 again was greatly decreased under these conditions.

The fact that the antigenic determinant recognized by Mab 126 is neither destroyed by trypsin nor by heat strongly suggests that it is carbohydrate in nature.

Figure 4:
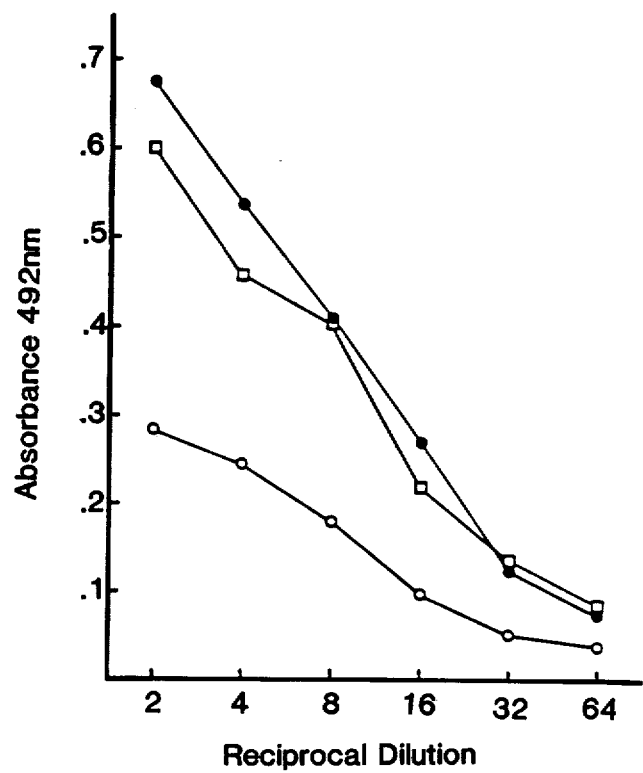
FIG. 4 is a graph of the results of an ELISA assay that illustrates the inhibition of binding at various dilutions of the monoclonal receptor of the present invention to LAN-2 cells by preincubation with a neuroblastoma glycolipid extract (o ---o). Pre-treatment of the glycolipid extract with sialidase eliminates the inhibition ( ---□). Binding of the monoclonal receptor preincubated with buffer but not with glycolipids was used as a control (●---●).

This is supported by the additional data illustrated in FIG. 4 that show that preincubation of 200 microliters of Mab 126 supernatant with glycolipid extracts from 40 micrograms of neuroblastoma tumor inhibited, by less than 50 percent, the binding to LAN-2 target cells in an ELISA assay. Furthermore, that inhibition could be eliminated by pre-treatment of the glycolipid extracts with sialidase, strongly suggesting that the antigen is a sialic acid-bearing glycolipid; i.e., a ganglioside.

Additional data indicating the gangliosidic nature of the antigen recognized by Mab 126 comes from inhibition of antibody binding studies. Specifically, preincubation of 200 microliters of Mab 126 supernatant, with an equivalent amount of nighly purified gangliosides isolated from the same neuroblastoma tumor, inhibited binding of the antibody to LAN-2 neuroblastoma cells from 38–51 percent at antibody dilutions ranging from 1:4 to 1:32. By way of contrast, these same purified gangliosides failed to inhibit binding of the anti-Thy-1 Mab 390 to LAN-2 cells. Taken together, these data indicate that the antigen recognized by Mab 126 is a ganglioside.

4. Quantitation of Ganglioside Antigen Expression by Fluorescence-Activated Cell Sorter (FACS) Analysis of Different Neuroblastoma and Melanoma Cell Lines A considerable heterogeneity in antigenic expression is known to exist among different neuroblastoma cell lines. The percentage of cells of different cell lines that express the antigen recognized by Mab 126 was determined using an excess of Mab 126 in an indirect immunofluorescence assay, followed by fluorescence-activated cell sorter analysis.

As summarized in Table III below, the antigenic determinant to which Mab 126 binds was present in 94-96 percent of the cells of neuroblastoma cell lines LAN-1, 2 and 5. By comparison, the Thy-1 antigen recognized by Mab 390, as reported in Seeger et al., J. Immunol., supra, was only present in 71-82 percent of the same neuroblastoma cells.

TABLE III

FACS Analysis of Positive Cells Among Various Neuroblastoma, Melanoma, and Lymphoblastoid Cell Lines.

| Test Reagent | Percent Positive Cells | | | | |
|---|---|---|---|---|---|
| | LAN-1 | LAN-2 | LAN-5 | M21 | LG2 |
| Mab 126 | 94-96 | 96 | 96 | 100 | 4-6 |
| Mab 390 | 80-82 | ND[1] | 71 | ND | ND |
| Mab W6/32 | 77 | ND | 10 | 100 | 100 |
| Mab 9.2.27 | ND | ND | ND | 100 | 4 |
| Non-immune X63 | 1-2 | 1 | 2 | | 3 |

[1]"ND" indicates binding not determined

Mab 126, as well as Mab 9.2.27, that is directed against a melanoma-associated proteoglycan [Bumol et al., Proc. Nat'l Acad. Sci. (USA), 79, 1245 (1982)] both recognized their corresponding antigen on 100 percent of M21 melanoma cells. In contrast, these respective antigens were expressed on only 4-6 percent of the B-lymphoblastoid cells LG2. It is noted that only 10 percent of the cells of the neuroblastoma cell line LAN-5 expressed HLA antigens, as determined by Mab W6/32, which is directed against a common structure present on all Class I histocompatibility antigens.

Figure 5:
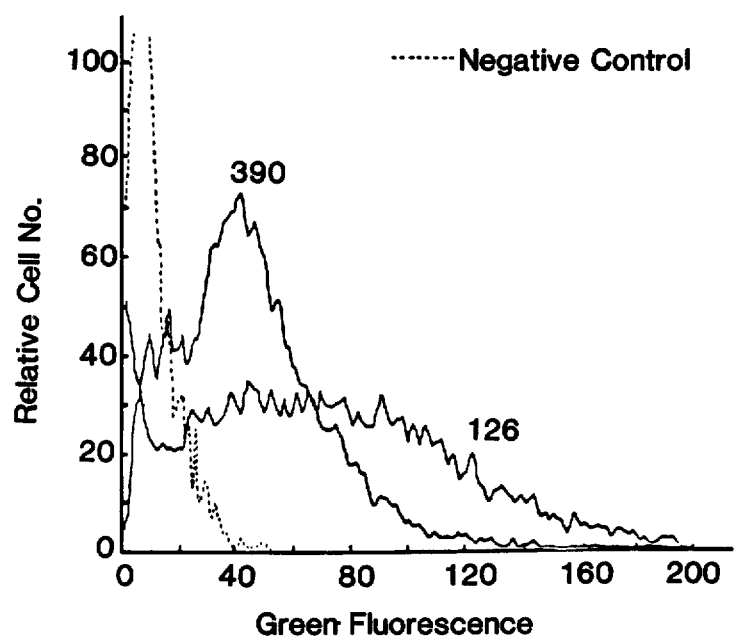
FIG. 5 is a graph from a fluorescent cell sorting study illustrating the heterogeneity of antigenic expression on LAN-1 neuroblastoma cells determined by reactivity with the monoclonal receptor of the present invention (Mab 126) and monoclonal receptor, Mab 390, respectively. Due to a significantly greater fluorescein fluorescence intensity, cells stained by monoclonal receptor Mab 126 were measured at one $\log_{10}$ lower gain.

The expression of the ganglioside antigen on LAN-1 neuroblastoma cells is illustrated by the results shown in FIG. 5. Using an excess of either Mab 390 or Mab 126 and the same amount of fluorescein-conjugated second antibody that binds to Mab 390 or Mab 126, the intensity of fluorescein bound to target cells was much higher with Mab 126 than with Mab 390. The increase in fluorescein fluorescence intensity due to Mab 126 binding was manifested by the need to decrease the gain of the cell sorter by one $\log_{10}$ (a factor of ten) for Mab 126 for the fluorescence emission to be within the same chart range as that produced by Mab 390. FIG. 5 also illustrates that the heterogeneity of expression of the ganglioside determined by Mab 126 is greater than that of the Thy-1 antigenic structure recognized by Mab 390.

The above results demonstrate that the monoclonal receptor of the present invention that is produced by a hybridoma formed by the fusion of a myeloma cell line and lymphocytes that produce antibodies that react with ganglioside $GD_2$ binds with ganglioside $GD_2$ A particular hybridoma used in producing a monoclonal receptor of the present invention (Mab 126) was deposited on May 25, 1984 in the American Type Culture Collection of Rockville, Md. and bears the designation ATCC HB 8568.

The above results also demonstrate that the diagnostic method of the present invention that utilizes the monoclonal receptor of the present invention is useful for assaying for the presence of ganglioside $GD_2$ on neuroectodermal tumor cells.

Several in vivo methods are also available for locating a neuroectodermal tumor having ganglioside $GD_2$ expressed thereon using an imaging technique. In such methods, a monoclonal receptor of the present invention is labeled with an indicator labelling means or "indicating group" or a "label". The indicating group or label is utilized in conjunction with the monoclonal receptor as a means for determining that ganglioside $GD_2$ has bound to the receptor. When a monoclonal receptor of this invention is utilized for the in vivo imaging of tumors, as discussed below, it is preferred that the idiotype-containing polypeptide portions (antibody binding sites) such as Fab and F(ab')$_2$ portions be used rather than whole, intact antibodies. The reason for this preference stems principally from the fact that the presence of Fc antibody portions from an animal species different from the animal whose tumor is to be imaged can lead to subsequent immunological complications.

The terms "indicator labelling means", "indicating group" or "label" are used herein to include single atoms and molecules that are linked to the receptor or used separately, and whether those atoms or molecules are used alone or in conjunction with additional reagents. Such indicating groups or labels are themselves well-known in immunochemistry and constitute a part of this invention only insofar as they are utilized with otherwise novel receptors, methods and/or systems.

The indicator labelling means can be a fluorescent labelling agent that chemically binds to antibodies or antigens without denaturing them to form a fluorochrome (dye) that is a useful immunofluorescent tracer. Suitable fluorescent labelling agents are fluorochromes such as fluorescein isocyanate (FIC), flourescein isothiocyanate (FITC), dimethylamino-naphthalene-S-sulphonyl chloride (DANSC), tetramethylrhodamine isothiocyanate (TRITC), lissamine rhodamine B200 sulphonyl chloride (RB 200 SC) and the like. A description of immunofluorescence analysis techniques is found in Marchalonis et al., "Immunofluorescence Analysis", 189-231, which is incorporated herein by reference.

The indicator labelling means can be linked directly to a receptor of this invention, to a useful antigen, or may comprise a separate molecule. It is particularly preferred that the indicator means be a separate molecule such as antibodies that bind to a receptor of this invention. Staphylococcus aureus protein A, sometimes referred to herein as protein A, may also be used as a separate molecule indicator or labelling means where an intact or substantially intact antibody receptor of this invention is utilized. In such uses, the protein A itself contains a label such as a radioactive element or a fluorochrome dye, as is discussed hereinafter.

The indicating group may also be a biologically active enzyme, such as horseradish peroxidase (HRP) or glucose oxidase, or the like. Where the principal indicating group is an enzyme such as HRP or glucose oxidase, additional reagents are required to visualize the fact that a receptor-ligand complex has formed. Such additional reagents for HRP include hydrogen peroxide and an oxidation dye precursor such as diaminobenzidine. An additional reagent useful with glucose oxidase is 2,2'azino-di-(3-ethylbenzthiazoline-6-sulfonic acid) (ABTS).

Radioactive elements provide another class of label, and are used herein as exemplary of useful labels. An exemplary radiolabelling agent that may be utilized in the invention is a radioactive element that produces gamma ray emissions. Elements that themselves emit gamma rays such as $^{125}I$ represent one class of gamma ray emission-producing radioactive element indicating groups. Another class of useful indicating groups are those elements such as $^{11}C$, $^{18}F$, $^{15}O$ and $^{13}N$ which themselves emit positrons. The positrons so emitted produce gamma rays upon encounters with electrons present in the animal's body.

A radioactive monoclonal receptor can be made by culturing in a medium containing radioactive amino acids, as is well known, as well as by isolating the monoclonal receptor and tnen labelling the monoclonal receptor with one of the above radioactive elements as described in U.S. Pat. No. 4,381,292.

The radiolabeled receptor such as Mab 126 or the idiotype-containing polypeptide portion thereof is then introduced as by injection into the blood stream of an animal having a neoplastic disease, especially a tumor. The labeled receptor forms a complex with the ganglioside $GD^2$ on the tumor cell surface, and after a suitable, predetermined time, such as about 18 to about 24 hours to permit clearance of unbound labeled receptor from the body, the animal or a portion is scanned.

The animal is scanned with a gamma ray emission counting machine such as the axial tomographic scanner commercially available under the designation CT (80-800 CT/T) from General Electric Company (Milwaukee, Wis.), or with a positron emission transaxial tomography scanner such as that designated Pett VI located at Brookhaven National Laboratory. Such scanning can provide an image of the tumor as well as information as to the location, size and shape of the tumor because of the specificity of the radiolabeled receptor utilized.

In another embodiment, Mab 126 is labeled with an indicating group containing an element that is active in nuclear magnetic resonance (NMR) spectroscopy; i.e., an NMR-active element. Many such elements are commercially available in useful form and are exemplified by $^{13}C$, $^{15}N$, $^{19}F$ and the like.

It is particularly preferred to utilize an indicating group containing the NMR-active $^{19}F$ atom, or a plurality of such atoms inasmuch as (i) substantially all of naturally abundant fluorine atoms are the $^{19}F$ isotope and thus substantially all fluorine-containing compounds are NMR-active; (ii) many chemically active polyfluorinated compounds such as trifluoroacetic anhydride are commercially available at relatively low cost, and (iii) many fluorinated compounds have been found medically acceptable for use in humans such as the perfluorinated polyethers utilized to carry oxygen as hemoglobin replacements.

Another particular advantage of the use of fluorine-containing NMR-active indicating groups is that the body contains very little fluorine under normal conditions. Consequently, by using an NMR-active element that is otherwise substantially absent from the animal, background signals due to bodily fluorine atoms are substantially absent. Thus, the principal signals observed are due to the labeled receptor—ganglioside $GD^2$ complex.

In this embodiment, a receptor sucn as Mab 126 is preferably labeled with a fluorine-containing material such as trifluoroacetic anhydride or hexafluoroethanol to form a fluorinated amide or ester derivative, respectively. Thereafter, the fluorinated receptor is introduced as by injection into the bloodstream of the tumor-containing animal. After a predetermined amount of incubation time for the labeled receptor to complex with the ganglioside $GD^2$ on the tumor cell surface, a so-called "whole-body" NMR determination is carried out using an apparatus such as one of those described by Pykett, *Scientific American*, 246, 78–88 (1982) to locate and form an image of the tumor.

Thus, the above methods of locating a neoplastic tumor in vivo in an animal include the steps of:

(a) providing a composition containing a receptor of the present invention wherein the receptor such as Mab 126 is bonded to an indicating group. Typical compositions include about 1 to about 100 milligrams of the labeled receptor in an aqueous medium such as that provided by water alone, an aqueous saline, phosphate-buffered saline or other aqueous buffer solution. The amount of receptor utilized depends, inter alia, upon the animal, the tumor size and the class of receptor, where an intact antibody is used. The useful indicating groups include gamma ray emission-producing elements, NMR-active elements and the like.

(b) The composition so provided is intoduced into the bloodstream of a neoplastic tumor-bearing animal, as by injection.

(c) The animal so injected is incubated for a predetermined period of time sufficient for the indicating group-bonded receptor to form an immunecomplex on the surface of the tumor, and preferably for non-bound, labeled receptor to clear from the animal's body.

(d) The animal is then scanned with a means for detecting the location of the complexed indicating group. Typical detecting means include usually used gamma ray emission detectors, those machines used in positron emission tomography and so-called "whole body" NMR spectrometers which may in practice only scan a portion of the body at any time.

Several in vitro methods are available for detecting the presence of ganglioside $GD_2$ in a sample to be assayed.

In one embodiment of tne invention, a solid assay method for detecting the presence of ganglioside $GD_2$ in a sample, that may be either (1) cells suspended in an aqueous medium such as PBS or (2) in a body fluid such as plasma or serum, to be assayed is contemplated. This method comprises the steps of: (a) providing a solid matrix on which to assay a sample; (b) admixing an aliquot of a liquid sample (cell suspension, plasma, serum or the like) to be assayed with the solid matrix to form a solid-liquid phase admixture; (c) maintaining the admixture for a predetermined time (typically about 10 to about 24 hours) sufficient for the sample to affix to the matrix and form a solid phase support; (d) separating the solid and liquid phases; (e) admixing a receptor of this invention with the separated solid phase to form a second solid-liquid phase admixture; (f) maintaining the second solid-liquid phase admixture for a predetermined time (typically about 0.5 to about 2 hours) sufficient for the receptor to immunocomplex with ganglioside $GD_2$ present in the sample; (g) separating the solid and liquid phases; and (h) determining the presence of ganglioside $GD_2$ that immunocomplexed with the receptor.

The presence of the ganglioside $GD_2$ that immunocomplexed with the receptor may be determined in a number of ways. In one preferred embodiment, that determination is made by the steps of (i) admixing a liquid solution containing an indicator labelling means (such as described hereinabove) with the solid phase obtained after step (g) above to form a third solid-liquid phase admixture, the indicator labelling means providing a means of detecting the presence of the receptor that reacted with ganglioside $GD_2$; (ii) maintaining the admixture for a predetermined time (typically about 0.5 to about 2 hours) sufficient for the indicator labelling means to immunocomplex with the receptor; (iii) separating the solid and liquid phases of the third solid-liquid phase admixture; and (iv) determining the presence of receptor that immunocomplexed with ganglioside $GD_2$.

The results of such an assay method for a cell suspension are shown in Table I discussed hereinbefore, and for serum in FIGS. 8 and 9 discussed hereinafter.

In yet another method, the presence of ganglioside $GD_2$ that immunoreacted with the receptor of the invention may be determined with the indicator labelling means being linked directly to the receptor. The presence of ganglioside $GD_2$ is determined by that label.

For example, the proteins present in a sample to be assayed may be radiolabelled with 125-iodine following one of the procedures described hereinafter. After separation of the solid and liquid phases of step (g), hereinbefore, the radiolabelled, but unbound, proteins are removed from the admixture thereby leaving radiolabelled, immunocomplexed ganglioside $GD_2$ on the solid support. The presence of that bound, radiolabelled ganglioside $GD_2$ can then be determined using a gamma counter. A similar result can be obtained using a reactive fluorescent molecule as the indicator labelling means such as fluoroscein isocyanate to react with the components of the assayed sample in place of the radioactive element.

In another embodiment of the invention, an assay method for detecting the presence of ganglioside $GD_2$ in a tissue sample to be assayed is contemplated. The method comprises the steps of: (a) providing a tissue sample to be assayed; (b) contacting the sample with the receptor of the invention that binds to ganglioside $GD_2$ for a predetermined time (typically about 0.5 to about 2 hours) sufficient for the receptor to react with ganglioside $GD_2$ present in the sample to form an immunocomplex; (c) contacting the immunocomplex with an indicator labelling means for a predetermined time (typically about 0.5 to about 2 hours) sufficient for the indicator labelling means to immunocomplex with the receptor, the indicator labelling means providing a means of determining the presence of receptor that reacted with ganglioside $GD_2$; and (d) determining the presence of receptor that reacted with ganglioside $GD_2$. The results from such an assay method are shown in Table II hereinabove.

Details for the above methods are given hereinafter wherein the indicator labelling means is peroxidase-labeled goat anti-mouse IgG+IgM or fluorescein-labeled goat anti-mouse antiserum, with peroxidase-labeled goat anti-mouse IgG+IgM being preferred. The aforementioned radiolabelling agents, fluorescent molecules and biologically active enzymes may also be utilized in the above method as indicator labelling means.

The presence of ganglioside $GD_2$ in a tissue sample may alternatively be determined by (i) combining the immunocomplex of step (b) above, after unreacted receptor is removed, with a second receptor that binds to the receptor of the invention for a predetermined time (typically about 30 minutes) sufficient for the second receptor to react with the receptor of the invention to form a second immunocomplex; (ii) contacting the second immunocomplex with a liquid solution containing (1) an indicator labelling means that provides a means of detecting the presence of receptor of the invention that reacted with ganglioside $GD_2$ and (2) a linking agent that links the indicator labelling means to the second receptor; and (iii) determining the presence of second receptor that reacted with the receptor-ganglioside $GD_2$ immunocomplex.

Details of the above method are given hereinafter wherein the second receptor is rabbit anti-mouse antibody, the indicator labelling means is a rabbit peroxidase anti-peroxidase complex antiserum and the linking agent is swine anti-rabbit antiserum. Any of the other indicator labelling means discussed hereinbefore can alternatively be utilized in the above method. Results from such an assay method are shown in FIGS. 1 and 2 discussed hereinbefore.

The monoclonal receptor of the invention may also be utilized in a diagnostic system for assaying for the presence of human neuroectodermal tumors. The system includes in at least one container (1) as an active ingredient, an effective amount of the monoclonal receptor of the invention in dry, solution or dispersion form. The system may also contain an indicating means, such as those described above, that when introduced into a sample, binds selectively with the monoclonal receptor.

The diagnostic system may also include a solid matrix that may be 96 well microtiter plates sold under the designation Falcon Microtest III Flexible Assay Plates (Falcon Plastics, Oxnard, Calif.) or a microtiter strip containing twelve wells in a row, such as those strips sold under the designation Immulon I and II (Dynatech, Alexandria, Va.). The microtiter strip or plate is made of a clear plastic material, preferably polyvinyl chloride or polystyrene. Alternative solid supports for use in the diagnostic system and method of this invention include polystyrene beads, about 1 micron to about 5 millimeters in diameter, available from Abbott Laboratories, North Chicago, Ill.; polystyrene tubes, sticks or paddles of any convenient size; and polystyrene latex whose polystyrene particles are of a size of about 1 micron and can be centrifugally separated from the latex.

The solid matrix may also be made of a variety of materials such as cross-linked dextran, e.g. Sephadex G-25, -50, -100, -200 and the like available from Pharmacia Fine Chemicals of Piscataway, N.J., agarose and cross-linked agarose, e.g. Sepharose 6B, CL6B, 4B, CL46 and the like also available from Pharmacia Fine Chemicals.

The diagnostic may further include a standard against which to compare the assay results and various buffers in dry or liquid form for, inter alia, washing the wells, diluting the sample or diluting the labeled reagent.

B. Cytotoxicity

The particularly preferred monoclonal receptor of the present invention, Mab 126, when mixed in an effective amount with a physiologically tolerable diluent, is suitable for use as a remedial composition for treatment of patients with neuroectodermal tumors. Thus, the administration of Mab 126 can provide a direct, anti-tumor cytotoxic effect.

The remedial composition containing the monoclonal receptor Mab 126 is administered in a unit dose having an effective amount of intact antibodies dispersed in a physiologically tolerable diluent such as serum, ascites, normal saline, water or phosphate-buffered saline. An effective amount of Mab 126 varies, inter alia, depending on the particular tumor cells treated and the amount of those cells. Generally about 1.5 milligrams to about 7.5 milligrams of Mab 126 per kilogram animal weight is considered effective.

The term "unit dose" refers to physically discrete units suitable as unitary dosages for animals, each unit containing a predetermined quantity of active material calculated to produce the desired therapeutic effect in association with the required diluent, i.e., carrier, or vehicle.

The discussion hereinafter describes effective amounts for in vitro uses, such as for clearing bone marrow of neuroectodermal tumor cells.

The capacity of Mab 126 to mediate complement dependent cytotoxicity (CDC) and antibody dependent cellular cytotoxicity (ADCC) in vitro were assessed since the cytotoxicity against tumor cells mediated by monoclonal receptors is important for clinical applications of such receptors.

1. Complement Dependent Cytotoxicity (CDC)

Figure 6:
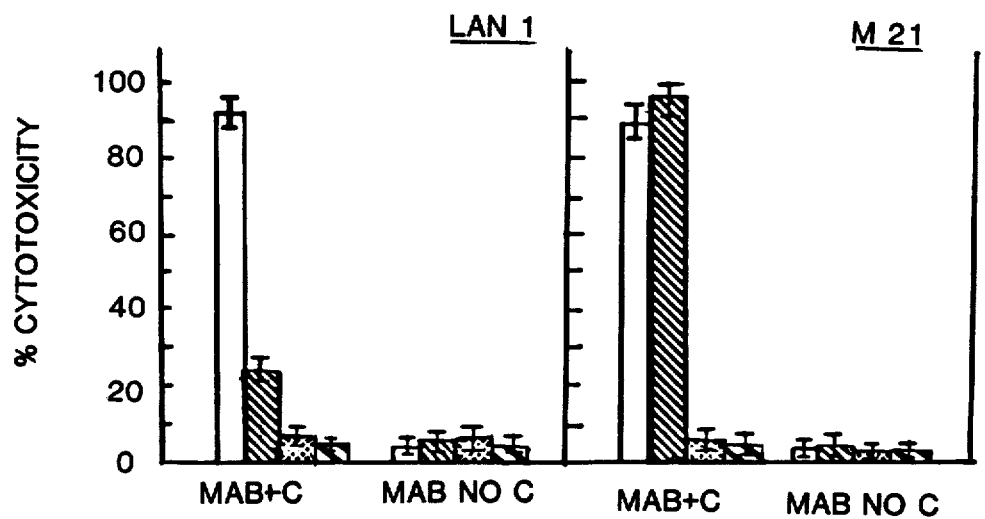
FIG. 6 illustrates the complement dependent cytotoxicity of various monoclonal receptors, including monoclonal receptor Mab 126 of the present invention. The columns dipict percent $^{51}Cr$ released from LAN-1 neuroblastoma and M21 melanoma cells induced by different monoclonal receptors with complement (Ab+C) and without complement (Ab no C). The monoclonal receptors utilizied for these studies were that of this invention, Mab 126, Mab W6/32 (an anti-HLA antibody) ▨, Mab 9.2.27 (an anti-melanoma-associated proteoglycan antibody) ■, and X63 ◿.

In a CDC assay using $^{51}$Cr-labeled target cells, Mab 126 proved to be highly efficient in mediating the killing of LAN-1 and M21 cells. As shown in FIG. 6, Mab 126, which strongly fixes complement, killed over 90 percent of these tumor cells in the presence of complement. Without complement, the cytotoxicity against these target cells did not exceed 2 percent.

It is of interest that, in the presence of complement, the anti-HLA Mab W6/32 mediated the killing of more than 90 percent of M21 melanoma cells, but only that of 25 percent of LAN-1 cells. This finding can be explained by a lower expression of Class I histocompatibility antigens on LAN-1 neuroblastoma cells as compared to that of M21 melanoma cells. On the other hand, Mab 9.2.27, which is known to be non-complement mediating, failed to specifically kill either M21 or LAN-1 targets.

Due to its high level of cytotoxicity to neuroblastoma cells, Mab 126 may also be useful for clearing bone marrow of tumor cells in vitro in combination with complement. Briefly, monoclonal receptor bound to polystyrene microbeads containing magnetite is used to remove tumor cells from bone marrow in vitro. A flow system using permanent samarium-cobalt magnets effects rapid and efficient removal of the tumor cells that have become magnetic from the magnetite of the bone marrow. See generally, Treleaven et al., *Lancet*, p. 70 (Jan. 14, 1984), and Kemshead et al., *Int. J. Cancer*, 27, 447 (1981).

In order to demonstrate that the complement-mediating killing of Mab 126 depends on the presence of its corresponding antigen on the target cell, the receptor was screened against the LG2 lymphoblastoid target cells in the same assay. The presence of the corresponding antigen was found to be required as Mab 126 with and without added complement did not induce a higher $^{51}$Cr release of these lymphoblastoid target cells than did the negative control antibodies 9.2.27 and X63, whereas the positive control antibody W6/32 was strongly cytotoxic.

The above results demonstrate that neuroectodermal tumor cells having ganglioside $GD_2$ expressed thereon are effectively killed by a composition of the present invention comprising an effective amount of Mab 126, complement and a physiologically tolerable diluent.

The neuroectodermal tumor cells are killed by contacting the cells with an effective amount of Mab 126 in the presence of complement. The contacting may be carried out in vitro by admixture of the neuroblastoma tumor cells and Mab 126.

The above results also demonstrate that tissues such as bone marrow may be cleared of tumor cells in vitro by contacting the cells with Mab 126 in combination with complement or a complement activator such as cobra venom factor.

2. Antibody-Dependent Cellular Cytotoxicity (ADCC)

The release of $^{51}$Cr induced by effector cells alone (normal killer cells) was 21 percent and 34 percent, respectively, when human mononuclear cells were used as effector cells in a 16 hour release assay against LAN-1 target cells at target:effector cell ratios of 1:100 and 1:200. When the target cells were pre-incubated with Mab 390, there was an additional specific $^{51}$Cr release of 19 percent and 22 percent at those two respective target:effector ratios. Preincubation of target cells with Mab 126 did not induce a higher specific release than that obtained with the X63 supernatant (3 percent). These results tend to indicate that Mab 126 is not capable of mediating antibody dependent cellular cytotoxicity against LAN-1 neuroblastoma cells.

3. Cytotoxic-Agent Linked Receptors

The above described remedial composition may additionally include a cytotoxic agent linked to the monoclonal receptor of this invention. The cytotoxic agent acts to kill the tumor cells in addition to any action provided by the receptor. Thus, the specificity of the receptor for locating and binding to tumor cells having ganglioside $GD_2$ expressed thereon is again utilized.

The cytotoxic agent utilized can be a drug such as adriamycin, the G-418 variant of neomycin, toxin molecules of plant or bacterial origin (immunotoxins), such as the bacterium *Corynebacterium diphtheriae* (diphtheria toxin) and the seeds of plants *Abrus precatorius* (abrin) and *Ricinis communis* (ricin), or the like. It is particularly preferred that the cytotoxic agent act at least in part by contact with tumor cell membranes.

Adriamycin is exemplary of a particularly preferred cytotoxic agent. The adriamycin is bonded to a receptor through its sugar ring-amino group via a dialdehyde such as glutaraldehyde, by a water-soluble carbodiimide or by other well known linking means. Tritton et al., *Science*, 217, 248–249 (1982) reported linking of adriamycin to agarose beads.

Those authors bonded the drug to the agarose beads as a means of contacting tumor cell membranes while avoiding general dissemination of the drug throughout the body tissues since adriamycin is known to have toxic effects upon the hearts of cancer patients. The cancer cells so contacted by Tritton et al. died.

It was suggested in an article appearing on page 69 of *Science News*, July 31, 1982 that a means other than the agarose beads would be needed for in vivo use on human patients. However, that suggestion was limited to one specific material, plasma membrane proteins, and did not include the use of the specific monoclonal receptor of the present invention inasmuch as monoclonal receptors such as those disclosed herein have not heretofore been available.

C. Serology Assays

Figure 7:
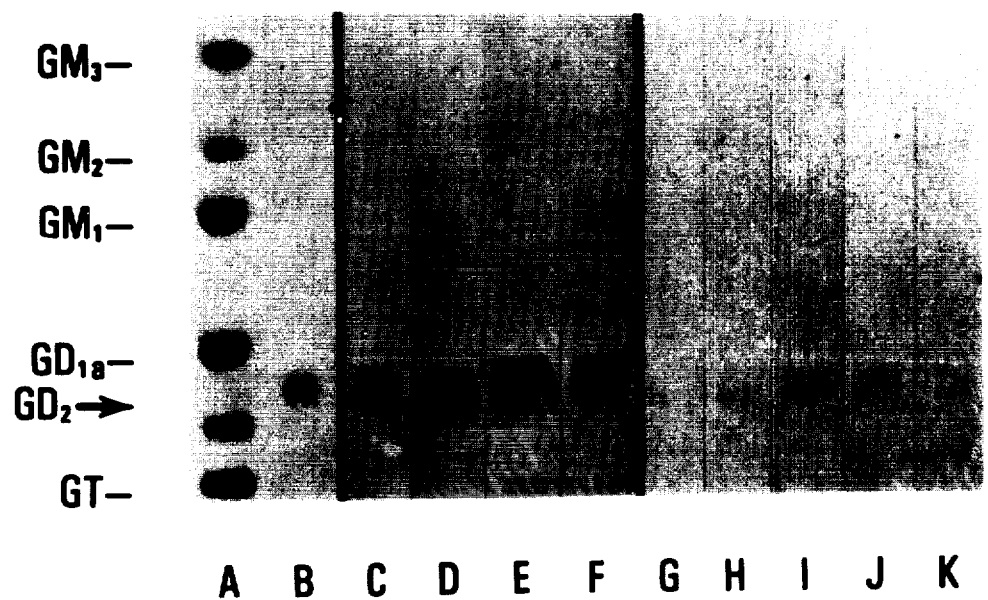
FIG. 7 illustrates the immunostaining of gangliosides separated on thin layer chromatography (TLC) by Mab 126. Lanes C-F show gangliosides extracted from sera of patients with neuroblastoma; Lanes G-K show gangliosides from sera of normal children; Lane B shows purified $GD_2$; and Lane A shows the migration of different ganglioside standards stained with resorcinol.

1. Reactivity of Mab 126 with Ganglioside Extracted from Serum Samples in an Immunostaining Procedure on TLC Screenings were undertaken to determine whether the $GD_2$ antigen could be detected in the circulation of a patient since relatively large amounts of this antigen are expressed in neuroblastoma tissues. In a first screening, gangliosides extracted from 750 microliters of serum were separated on a TLC plate and immunostained to assess the binding of Mab 126 to $GD_2$ by an ELISA procedure. FIG. 7 clearly shows that $GD_2$ present in the sera of four patients with neuroblastoma (Stage IV and IVs) reacted strongly with Mab 126 (lanes C-F), whereas control serum samples from four normal children showed only faint staining (lanes G-K). The reactivity of Mab 126 with purified $GD_2$ is demonstrated in lane B, while lane A shows the migration of different ganglioside standards stained with resorcinol. When the same gangliosides were separated on TLC and sprayed with resorcinol instead of using the immunostaining procedure, only the neuroblastoma patients' ganglioside profile revealed a prominent $GD_2$ band (data not shown).

These data demonstrate that neuroblastoma patients have relatively large amounts of circulating $GD_2$ in serum. Therefore, a quantitative assay was developed to determine the exact levels of $GD_2$ in the sera of patients and control individuals.

2. $GD_2$ Levels in Sera from Neuroblastoma Patients, Children with Other Pediatric Tumors and Normal Children In earlier screenings, it was shown that the binding of Mab 126 to neuroblastoma or melanoma cells is specifically inhibited by preincubation with purified $GD_2$. In order to determine the amount of $GD_2$ extracted from serum samples, the inhibition of binding of Mab 126 induced by different amounts of purified $GD_2$ was calculated.

Figure 8:
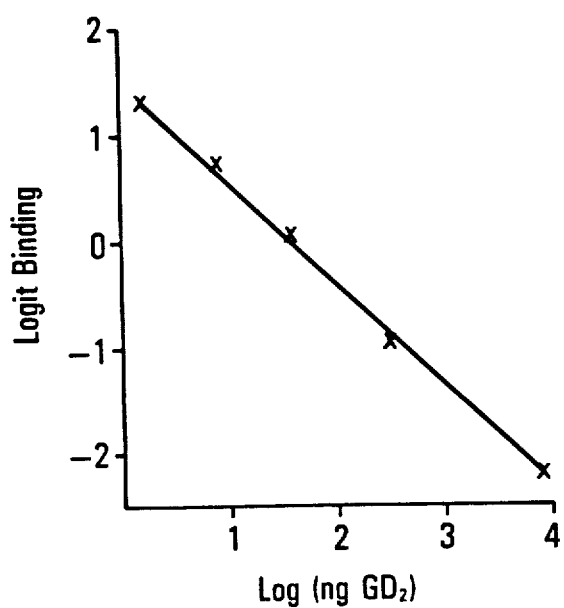
FIG. 8 illustrates the inhibition of Mab 126 binding to $GD_2$-containing glycolipids in ELISA after preincubation with different amounts of purified $GD_2$ [2.5–50 nanograms (ng)]expressed in a log vs. logit plot.

FIG. 8 shows the results from one representative screening. Mab 126 supernatant was preincubated with purified $GD_2$, ranging in concentration from 2.5-50 nanograms. These supernatants were then evaluated in duplicate in ELISA against glycolipids containing a large amount of $GD_2$. The binding was compared to that obtained with antibody supernatant that was not preincubated with $GD_2$ and the data expressed in a log logit plot. The correlation coefficient of the standard plot was 0.98. Using these data, the amount of $GD_2$ in semi-purified gangliosides extracted from serum samples could be determined by the inhibition they induced in this competitive ELISA. Whenever the inhibition was outside of the range of sensitivity of the standard curve, samples were retested at higher dilutions. Because the recovery in the extraction procedure was greater than 93 percent in the two studies conducted (data not shown), these values were considered to be essentially the same as the actual amount of $GD_2$ in serum.

Figure 9:
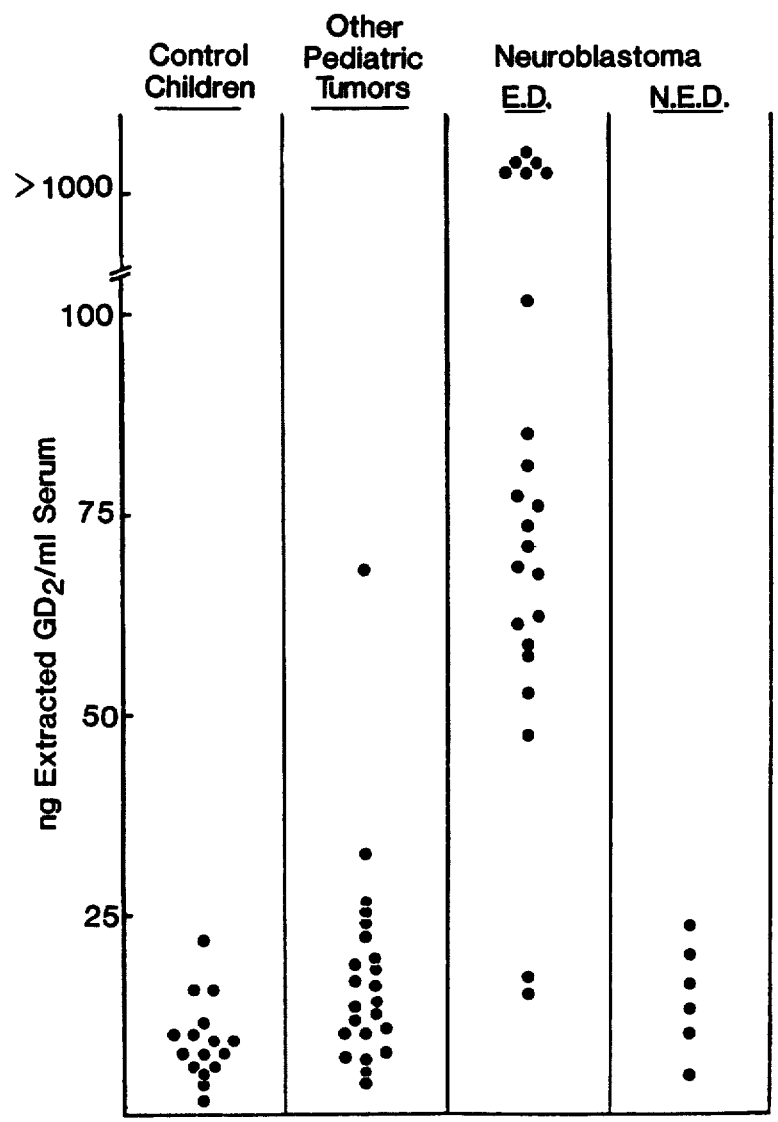
FIG. 9 illustrates levels of GD$_2$ (ng/ml) extracted from sera of patients with neuroblastoma (E.D.=evidence of disease; N.E.D.=No evidence of disease), children with other tumors and control children. Values were determined by competitive ELISA.

FIG. 9 shows the serum levels of $GD_2$ determined by the competitive ELISA in patients with active neuroblastoma (N23), other pediatric tumors (N23), healthy, age-matched controls (N16), and patients with non-active neuroblastoma (N6). The mean age of neuroblastoma patients was $61 \pm 55$ months compared to $63 \pm 38$ months in children with other tumors, $65 \pm 48$ months in normal controls and $42 \pm 24$ months in patients with non-active neuroblastoma.

Three neuroblastoma patients evidenced stage IVs, 8 had stage IV, 6 had stage III, 3 had stage II, and 3 had stage I neuroblastomas. The patients who after therapy showed no clinical signs of neuroblastoma were originally classified as stage IVs (2), stage IV (2), stage II (1), and stage I (1).

Patients with other tumors had the following diagnoses: rhabdomyosarcoma (4), Ewing's sarcoma (2), Wilms' tumor (3), osteogenic sarcoma (2), Hodgkin's disease (2), mesenchymoma (1), histiocytosis X (1), retinoblastoma (1), acute lymphoblastic leukemia (4), acute myeloblastic leukemia (1), non-Hodgkin's lymphoma (1), and Burkitt's lymphoma (1).

Data depicted in FIG. 9 indicate that 21 of 23 neuroblastoma patients exhibited $GD_2$ levels in serum of more than 26 ng/ml [mean of controls $+3$ standard deviation (S.D.)]indicating a degree of accuracy of greater than 99.8 percent. The two neuroblastoma patients with lower levels had disease classified as stage I and II. Of six patients with very high $GD_2$ levels (over 1000 ng/ml), 4 had stage IV and 2 had stage III. One of these patients even had a $GD_2$ level of 4300 ng/ml.

Because the number of neuroblastoma patients with stage I and II was very small, the $GD_2$ levels of patients with different stages of disease were not compared. However, none of the neuroblastoma patients with stage I and II had $GD_2$ serum levels above 100 ng/ml. Among patients with other tumors, only two showed elevated $GD_2$ levels in serum. One child had a Wilms' tumor (69 ng/ml) and the other had an oseogenic sarcoma (33 ng/ml). It is interesting that two other patients with Wilms' tumor as well as one other child with osteogenic sarcoma exhibited normal levels of $GD_2$ in their sera.

Six children who after treatment were considered to be free of tumor showed normal levels of $GD_2$ in their serum. The mean $GD_2$ serum level of these children ($\bar{x} = 14.8 + 6.8$ ng/ml) was similar to that of normal controls ($\bar{x} = 8.8 + 5.8$ ng/ml) and children with other tumors ($\bar{x} = 18.2 + 13.6$ ng/ml).

When the $GD_2$ levels were compared in a ranking evaluation test corresponding to Wilcoxon-Mann-Whitney [see for example, Box et al., "Statistics for Experimenters", John Wiley & Sons, New York, pp. 80-82 (1978)], the difference in serum $GD_2$ levels of patients with neuroblastoma compared to all other groups was statistically highly significant (p of less than 0.001). However, there was no statistically significant difference among the three other groups; i.e., normal individuals, patients without clinical evidence of neuroblastoma and patients with other tumors.

For control purposes, these same neuroblastoma sera extracts were preincubated with a Mab directed against $GD_3$; i.e., MB3.6 (not reactive with neuroblastoma tissues), and it was found that its binding was not inhibited in this assay (data not shown). These data demonstrate that the inhibition of Mab 126 with these sera extracts is specific.

In addition, in one patient, the serum level of $GD_2$ during the clinical course of disease was monitored. This two year old child had neuroblastoma stage III witn infiltration of the tumor to kidney, bone, and thoracic fluid. Tne $GD_2$ serum level before treatment was 1600 ng/ml. After the first chemotherapeutic cycle with cyclophosphamide and vincristine, there was a good clinical response with tumor regression. The $GD_2$ level correspondingly fell to 148 ng/ml. Two months later, after two additional therapy cycles, the patient was still in partial remission.

The observable decrease in $GD_2$ level remained constant and thus correlated with this patient's response to therapy. These data indicate that the level of $GD_2$ in serum is a useful indicator for tumor regression and reoccurrence in neuroblastoma. Thus, Mab 126 is particularly useful in the immunoperoxidase assay to discriminate between neuroectodermal tumor cells and normal tissues, especially as, in contrast to many other tumor-associated antigens, the $GD_2$ ganglioside antigen recognized by Mab 126 is not denatured by the routinely used formaldehyde fixation of tissues. This characteristic enhances the usefulness of this receptor for clinical applications, such as the diagnosis, monitoring and treatment of neuroectodermal tumors.

III. MATERIALS AND METHODS

A. Cell Lines

The following cell lines were used for screening of the monoclonal receptor of the present invention; sources for each line are parenthesized following the cell line designation: neuroblastoma: LAN-1, 2, 5 (Dr. R. Seeger, University of California at Los Angeles, hereinafter UCLA); SK-N-SH, American Type Culture Collection, Rockville, Md. (ATCC HTB 11); melanoma: M14, M21 (Dr. D. Morton, UCLA); FM3, FM8, F12 (Dr. J. Harper, Scripps Clinic, La Jolla, Calif.); Mueller (Dr. P. Koldovsky, Dusseldorf, W. Germany); Foss (Dr. B. Giovanella, Stehlin Foundation, Canc. Res., Houston, Tx.); glioma: U373 MG, U138 MG, U87 MG (ATCC HTB 17, ATCC HTB 16, ATCC HTB 14, respectively); small cell carcinoma of lung: H69 (Dr. J. Minna, NCI, Bethesda, Md.); B-lymphoblastoid: LG2, L14 (Dr. Gati, UCLA); leukemias: Molt-4 (ATCC CRL 1582), HPB-All, Burkitt lymphoma Daudi (ATCC CCL 213); adenocarcinoma of lung: T291 (Drs. Masue and Sato, University of California at San Diego, hereinafter UCSD); UCLA-P3 (Dr. D. Morton, UCLA); squamous cancer of skin: SCI-I185; anaplastic cancer: CALU-6 (ATCC HTB 56); adenocarcinoma adrenal cortex: SW13 (ATCC CCL 105); Wilms' tumor: WIL-TU-1 (ATCC HTB 50): osteosarcoma: U-20S (ATCC HTB 96); Ewing sarcoma: SK-ES-2 (ATCC HTB 87); Rnabdomyosarcoma: A204 (ATCC HTB 82).

B. Monoclonal Receptors

Monoclonal receptor 126 was produced by immunization with the neuroblastoma cell line LAN-1 using the standard hybridoma technology of Kohler et al., *Nature*, 256, 495 (1975). Briefly, BALB/c mice were immunized by injection once every week for a total of 4 weeks with $5 \times 10^6$ LAN-1 neuroblastoma cells, their splenocytes were removed and a suspension of the splenocytes was made. The splenocytes were then fused three days after the last injection with the murine myeloma cell line P3X63Ag8 in the presence of a cell fusion promoter (polyethylene glycol 2000) to form hybridomas. Hybridoma 126 was selected by growth in Dulbecco's Modified Eagle's Medium (DMEM) containing 10 percent fetal calf serum (FCS), Hypoxanthine, Aminopterin and Thymidine; i.e., (HAT) medium, that will not support growth of the unfused myeloma cells, and was subcloned using limiting dilution and culturing in separate containers. The resulting supernatant in each container was evaluated for the presence of the isotype of the Mab 126 with a Litton Bionectics Kit (Litton Bionectics, Kenginston, Md.) as described in the kit instructions. The desired hybridoma was selected and cloned, and Mab 126 was recovered from the supernatant above the clones.

In addition, the following Mabs were used: Mab 9.2.27 directed against a chondroitin sulfate proteoglycan on melanoma cells, [Bumol et al., *Proc. Nat'l Acad. Sci. (USA)*, supra]; Mab 390 directed against Thy-1 antigenic structure present on neuroblastoma cells as reported in Seeger et al., *J. Immunol*, supra, Mab MB3.6, directed against the ganglioside antigen GD$_3$ [Koprowski, et al., *Science, supra*], and Mab W6/32, recognizing the common structure of HLA antigens, were provided by Dr. Seeger of UCLA and Dr. Parham of Stanford University, Stanford, Calif., respectively.

Alternatively, the monoclonal receptor of the present invention may be produced by introducing, as by injection, the hybridoma into the peritoneal cavity of a mammal such as a mouse. Preferably syngenic or semi-syngenic mammals such as mice are used, as in U.S. Pat. No. 4,361,549, whose illustrative teachings of which are incorporated herein by reference. The hybridoma introduction causes formation of antibody-producing hybridomas after a suitable period of growth, e.g. 1–2 weeks, and results in a nigh concentration of the receptor being produced that can be recovered from the bloodstream and peritoneal exudate (ascites) of the host mouse. Although these host mice also have normal receptors in their blood and ascites, the concentration of normal receptors is only about five percent that of the monoclonal receptor concentration.

The monoclonal receptor present in hybridoma supernatants is used without purification or can be recovered from the ascites or serum of the mouse using standard techniques such as affinity chromatography using LAN-1 cells bound to an immunosorbant such Sepharose 6B or 4B (Pharmacia Fine Chemicals, Piscataway, N.J.), followed by elution from the immunosorbant using an acidic buffer such as glycine hydrochloride at a pH value of about 2.5.

C. Tissues

Portions of fresh normal and malignant tissues were obtained from the surgical pathology department of the Ida M. Green Hospital of Scripps Clinic, La Jolla, Calif. Other tumor samples were kindly provided by Drs. F. Kung and A. Yu (Dept. of Pediatric Oncology, UCSD) and by Dr. P. Wolf (Dept. of Pathology, UCSD). Fresh tissue specimens were embedded in Tisssue Tek-II O.C.T (Miles, Naperville, Ill.), frozen in blocks in isopentane at liquid nitrogen temperature, and then stored at $-70°$ C. Formalin-fixed paraffin embedded blocks were obtained from the files of the Department of Pathology, UCSD.

D. Immunoperoxidase Staining of Frozen Tissues

Sections of frozen tissue blocks, 4–6 microns thick, were cut on a microtome cryostat, mounted on glass slides, briefly air-dried, and either stained immediately or stored at $-70°$ C. in airtight boxes. An indirect immunoperoxidase assay, similar to that described by Taylor, *Path. Lab. Med.*, 102, 113 (1978), the teachings of which are incorporated herein by reference, was used to stain these slides. Briefly, after washing in phosphate buffered saline (PBS), pH 7.1, the sections were preincubated (contacted) for 15 minutes at room temperature in PBS containing 10 percent goat serum and 0.1 percent bovine serum albumin to block non-specific binding sites. Excess serum was then removed by aspiration, and appropriately diluted monoclonal receptor supernatant was overlayed onto the sections to contact the tissues. That contact was maintained in a humid chamber for one hour, and was followed by a brief wash in PBS. The washed tissues were thereafter contacted with a 1:50 dilution of peroxidase labeled goat anti-mouse antibody (IgG +IgM; Tago, Burlingame, Calif.) to bind the labeled goat anti-mouse antibody to the receptor of this invention, Mab 126. This contact was maintained for a one hour time period at room temperature, and was then followed by a rinse in PBS.

The brown color reaction provided by the peroxidase label was developed with 0.6 milligrams/milliliter (mg/ml) of diaminobenzidine in 0.03 percent $H_2O_2$. After counterstaining with 1 percent methylene blue, the slides were washed in water and dehydrated in isopropyl alcohol. They were then cleared in xylene, mounted in parmount, coverslipped and examined using an American Optical Microstar Series 20 microscope to determine wnich tissue areas, if any, were stained by the dye produced by the diaminobenzidine.

E. Paraffin-Embedded Tissues

The procedure was slightly modified from that already described in Taylor, *Path. Lab Med.*, *supra.* Briefly, sections on gelatin coated slides were deparaffinized and rehydrated. After an initial incubation with 0.3 percent $H_2O_2$ to block endogenous peroxidase, Mab 126 diluted 1:100 in 1 percent bovine serum albumin (BSA) in PBS (pH 7.6) was then applied to the sections to contact the tissue with the receptor. The tissue and receptor were maintained in contact for a period of 30 minutes at room temperature in a humid chamber to permit binding to occur. The slides were rinsed in PBS and a second antibody; i.e., rabbit anti-mouse at a dilution of 1:1000 in BSA-PBS, was incubated (contacted) with the sections for 30 minutes at room temperature to bind the anti-mouse antibodies to the mouse antibodies.

Swine anti-rabbit antiserum (1:100) and rabbit peroxidase anti-peroxidase complex antiserum (1:1000) were added sequentially to the sections. The rabbit peroxidase anti-peroxidase complex is linked by the swine anti-rabbit antiserum, acting as a linking agent, to the rabbit anti-mouse antibody. The rabbit anti-mouse antibody is, in turn, combined with the unlabeled Mab 126 which reacts with ganglioside $GD_2$ antigen in the tumor tissues. The sections were then rinsed with PBS after each incubation period of 30 minutes. The color reaction was developed, the sections dehydrated, cleared in xylene, mounted and viewed as described above.

F. Enzyme-linked Immunosorbent Assay (ELISA)

Target cells to be assayed were washed and resuspended in PBS, and were then plated in flat-bottom polyvinyl chloride microtiter plates (Dynatech, Alexandria, Va.) at $5 \times 10^4$ cells per well using 50 microliters of sample composition. The plates were then incubated overnight at 37° C. in a dry oven. The dried plates were stored at 4° C. until use. Prior to the ELISA assay, dried plates were rehydrated by two washes of 2 minutes each with 10 millimolar (mM) PBS, pH 7.4, containing 0.1 percent polyoxalkylene (20) sorbitan monolaurate (Tween 20) and 0.02 percent Thimerosal (sodium ethylmercurithiosalicylate) (Sigma, St. Louis, Mo.).

In order to reduce non-specific binding, hybridoma supernatants were diluted 1:2 in washing buffer containing 0.1 percent BSA as diluent. Fifty microliters of diluted hybridoma supernatants were thereafter added to each well and incubated for 1 hour at 4° C. on a gyroshaker to contact the Mab 126-containing supernatant with the assayed cells and to bind the receptor to its ganglioside ligand. Following two washes of 2 minutes each, 50 microliters of peroxidase-labeled goat anti-mouse IgG+IgM (Tago, Burlingame, Calif.), diluted 1:1000, were added to each well, and the reaction mixture was incubated at 4° C. for 1 hour to bind the labeled antibody to bound Mab 126.

The substrate used to assay bound peroxidase activity was prepared just prior to use and consisted of 400 microgram/ml o-phenylenediamine (Sigma, St. Louis, Mo.) in 80 mM citrate-phosphate buffer, pH 6.0, containing 0.12 percent $H_2O_2$. After two final washes, 50 microliters of substrate solution was added to each well and color was allowed to develop for 15 minutes in the dark. Color development was stopped by adding 25 microliters of 4 molar (M) $H_2O_2$ to each well and the optical absorbance at 492 nanometers (nm) was measured with a Multiskan ELISA plate reader.

G. Indirect Immunofluorescence Assay

Unfixed tissue culture cells ($10^6$) were washed in PBS and tnen centrifuged in an Eppendorf centrifuge. After removing the washing fluid, the cells were resuspended in 50 microliters of Mab supernatant to contact the cells with the antibody. The cell-antibody admixture thus formed was maintained for a period of 45 minutes on ice to bind the receptors to the cells, and was then centrifuged ($200 \times g$) through 2 ml FCS.

Thereafter, any unbound antibody and FCS were removed: The cell sediment was resuspended with 50 microliters of fluorescein-labeled goat anti-mouse antiserum diluted 1:50 (Tago, Burlingame, Calif.) and incubated another 45 minutes on ice to contact and bind the labeled anti-mouse antibodies to the bound Mab 126 receptors. After removing any unbound second antibody as described above, the cells were fixed with 1 percent formaldehyde in PBS. Cell-bound fluorescein was determined by using a fluorescence activated cell sorter (FACS) (Cytofluorograf, Ortho Diagnostics, Westwood, Mass.).

H. Antibody-Dependent Cellular Cytotoxicity (ADCC)

Tumor target cells were labeled with $^{51}Cr$ (sodium chromate at 1 milliCurie/milliliter (mCi/ml), New England Nuclear, Boston, Mass.). Routiely, $2 \times 10^6$ cells were incubated with 100 microCi $^{51}Cr$ for 1 hour at 37° C. in RPMI culture medium 1640 (Roswell Park Memorial Institute, Buffalo, N.Y.) containing 10 percent FCS. The radiolabeled cells were washed three times, resuspended in RPMI 1640 and 10 percent FCS, and were plated in 96-well round bottom tissue culture plates (Costar, Cambridge, Mass.) at $10^4$ cells/well.

The target cells so prepared were then treated with antibodies by admixture with 50 microliters of Mab supernatant to contact tne cells with the antibodies. Contact was maintained for an incubation period of 60 minutes.

Following the incubation, the plates were centrifuged in their entirety at 45xg for 2 minutes and the supernatant fluids containing unbound receptor were removed and discarded. Human mononuclear cells purified over a Ficoll-Hypaque gradient served as effector cells. These cells were then added to the Mab-treated target cells at various target:effector cell ratios in a final volume of 200 microliters. All cultures were initiated in triplicate, and were maintained by incubation at 37° C. in 5 percent $CO_2$ for 16 hours. Tnereafter, the plates were centrifuged at $170 \times g$ for 4 minutes, 100 microliters of each supernatant was removed and the radioactivity measured in a Packard gamma counter. The cell mediated killing of the target cells was calculated as follows:

percent lysis =

$$\frac{\text{Experimental cpm} - \text{spontaneous cpm}}{\text{maximum release cpm} - \text{spontaneous cpm}} \times 100$$

In this equation, spontaneous cpm (counts per minute) represents the radioactivity released from target cells in the absence of effector cells. Maximum release was determined by treating the target cells with the non-ionic detergent NP 40 [(polyoxyethylene (9) octyl phenyl ether; Shell Oil Company)]at a concentration of 1 percent in PBS.

I. Complement Dependent Cytotoxicity Assay

Labeling of tumor target cells with $^{51}$Cr and preincubation with Mab supernatant (50 microliters) was done as described for the ADCC. Instead of effector cells, 100 microliters of rabbit serum were added, diluted 1:8 in RPMI medium 1640, serving as a complement source. After a 2 hour incubation at 37° C., the plates were centrifuged at 170×g for 4 minutes and 100 microliters of supernatant removed. The killing of the target cells was calculated as described above.

J. Glycolipid and Ganglioside Preparation

A total lipid extract was prepared from 2 grams (gm) of freshly isolated neuroblastoma tissue by homogenization in 40 milliliters (ml) of chloroform:methanol (2:1) and followed by filtration through a scintered glass filter. The residue was re-extracted with chloroform:methanol (1:1) and re-filtered. The combined filtrates were then subjected to rotary evaporation. The dried glycolipid extract was dissolved in 10 ml of chloroform:methanol, (2:1). Gangliosides were partitioned into an aqueous phase as described by Ledeen et al., *Methods in Enzymol.*, 83, 139 (1982), the teachings of which are incorporated herein by reference. Tnis material was dialyzed exhaustively against cold distilled water and lyophilized.

The lyophilized crude ganglioside preparation was dissolved in 20 ml of methanol-chloroform-water (60:30:8) and applied slowly to a column (1 cm×15 cm) of DEAE-Sepharose CL-6B (Pnarmacia Fine Chemicals, Piscataway, N.J.). The column was washed extensively with the above solvent and gangliosides were eluted with methanol-chloroform containing 0.8 M aqueous sodium acetate (60:30:8). Fractions were collected and assayed for the presence of gangliosides by thin layer chromatography (TLC), as described hereinafter, using a variety of ganglioside standards. Fractions containing gangliosides were evaporated and dissolved in distilled H$_2$O to be dialzed and lyophilized.

The freeze-dried material was dissolved in chloroform:methanol (1:1) and applied to a column of Iatrobeads [poly(iso-butyl methacrylate) beads](Polyscience, Inc., Warrington, Pa.) as described by Ledeen et al., cited above. The material eluted from this column was relatively free from contaminants.

K. Sialidase Treatment of Neuroblastoma Glycolipids and Innibition of Antibody Binding to Neuroblastoma Targets A glycolipid extract obtaining from 40 micrograms of tumor tissue was dried under nitrogen, resuspended in 200 microliters of 0.05 M sodium acetate buffer, pH 5.3, continuing 9 mg/ml NaCl, 1 mg/ml CaCl$_2$, 2 units of *Clostridium perfringens* sialidase (type x; Sigma, St. Louis, Mo.) and incubated at 37° C. for 1 hour. A control sample was incubated in parallel in buffer alone. The reaction was stopped by the adition of 1 ml chloroform:methanol (2:1), followed by evaporation to dryness.

Mab 126; i.e., 200 microliters of hybridoma supernatant, was added to the dried sialidase treated neuroblastoma lipid extract, as well as to the control sample, and allowed to incubate for 1 hour at room temperature. The reaction mixture was then centrifuged at 1000×g for 5 minutes. The receptor was diluted appropriately and assayed for binding to neuroblastoma cell targets by ELISA.

L. Serum Samples

Serum samples were provided by Dr. A. Lightsey (Dept. of Pediatric Oncology, Navy Hospital, San Diego, Calif.), Dr. F. Lampert (Dept. of Pediatric Oncology, Justus Liebig University, Giessen, W. Germany), Dr. Castleberry (Dept. of Pediatric Oncology, Birmingham, Ala.), and the Department of Pediatric Oncology, University of California, San Diego. All serum samples were drawn before intense chemotherapy of patients was started. They were frozen and stored at −20° C. until used in the assay. In all cases, the clinical diagnosis was confirmed by histology.

M. Purification of Ganglioside from Serum Samples

Serum samples were dissolved in chloroform:methanol (2:1) at a ratio of 1:20 (vol/vol) and filtered through syringes filled with scrubbed nylon fiber (3 denier, 3.81 cm, type 200, Fenwal Laboratories, Deerfield, Ill.) to remove protein aggregates. The residues were re-extracted with chloroform:methanol (1:1) at a ratio of 1:20 (vol/vol). The combined filtrates were then subjected to nitrogen evaporation. The dried glycolipid extract was dissolved in 5 ml of chloroform:methanol (2:1). Gangliosides were partitioned into an aqueous phase as described by Leeden et al., *Methods in Enzymol.*, supra. This material was dialyzed exhaustively against cold distilled water and dried down by rotary evaporation.

N. Ganglioside Standards

Purified ganglioside standard GD$_2$ was kindly supplied by Dr. R. K. Yu (Yale University, New Haven, Conn.). Gangliosides GM$_3$ and GM$_2$ were supplied by Dr. J. Sundsmo (Scripps Clinic, La Jolla, Calif.), and gangliosides GM$_1$, GD$_{1a}$ and GT were purchased from Supelco (Bellefonte, Pa.).

O. Thin Layer Chromatography (TLC)

Silica gel plates (plastic backed, E. M. Merck, Darmstadt, W. Germany) were activated by heating at 110° C. for 1 hour. Chloroform:methanol/0.2 percent aqueous CaCl$_2$ (60:45:10) was used for the development of the chromatograms. Samples were spotted 1.5 cm from the bottom of the TLC plates that were then placed in a developing tank presaturated with 100 ml of the above solvent. Chromatograms were developed for 1.5 hours at room temperature, after which the plates were allowed to dry. Appropriate lanes of chromatograms were cut and sprayed with resorcinol reagent to visualize gangliosides as described in Jourdian et al., *J. Biol. Chem.*, 246, 430 (1971).

P. Immunostaining of Gangliosides Separated by TLC

The reactivity of Mab 126 with ganglioside separated by TLC was determined directly by using an immunostaining method originally described by Magnani et al., *Anal. Biochem.*, 109, 399 (1980). This procedure was modified by using an ELISA detection system.

Q. Lipid ELISA Inhibition Assay

For the preparation of lipid plates, a total lipid extract was prepared from 2 ml of packed Melur melanoma cells, that are known to express the $GD_2$ ganglioside. These cells were homogenized in 40 ml chloroform:methanol (2:1), followed by filtration through a scintered glass filter. The residue was re-extracted with chloroform:methanol (1:1) and re-filtered. The combined filtrates were then dried down. Finally, these glycolipids were resuspended in methanol. Routinely, glycolipids from a 50 nanoliter packed cell volume were plated per well in flat-bottom polyvinyl microtiter plates (Dynatech, Alexandria, Va.). Before use in the assay, the plates were preincubated for 2 hours with 1 percent BSA in PBS.

The assay to detect $GD_2$ was done by incubating 100 microliters of Mab 126 supernatant for 1 hour at room temperature with semi-purified gangliosides extracted from different serum samples (300 microliters). After centrifugation for 5 minutes in an Eppendorf centrifuge, 75 microliters of this supernatant was diluted 1:4 and 50 microliters of the diluents were evaluated in duplicate for binding to the lipid plates in ELISA. The ELISA assay was similar to that for cultured cell lines described above except that 1 percent BSA in PBS was used as washing and diluting buffer. Binding of antibody preincubated with partially purified gangliosides obtained from serum samples was compared to that achieved with antibody binding alone when incubated with lipid plates.

In addition, the inhibition of antibody achieved with different serum samples was compared to that obtained by preincubation of antibody with different amounts of purified $GD_2$. By using a log-logit binding curve, it was possible to determine the amount of $GD_2$ in both patient and control sera.

R. Statistical Evaluation

The differences of $GD_2$ levels in sera from different patient groups and control individuals were evaluated for statistical significance using the Rank Testing according to Wilcoxon-Mann-Whitney (see for example, Box et al., "Statistics for Experimenters", supra).

The foregoing is intended as illustrative the present invention but not limiting. Numerous variations and modifications may be effected without departing from the true spirit and scope of the invention.

What is claimed is:

1. A non-human, mammalian monoclonal receptor produced and secreted by a hybridoma having the ATCC accession number HB 8568 and reacting the ganglioside $GD_2$.

2. The monoclonal receptor of claim 1 wherein said receptor is an intact antibody.

3. The monoclonal receptor of claim 1 wherein said receptor is the F(ab')₂ portion of an antibody.

4. A hybridoma having the ATCC accession number 8568 that produces and secretes a monoclonal receptr that reacts with ganglioside $GD_2$.

5. A diagnostic system for assaying for the presence of gangliside $GD_2$, said system including in at least one container, as an active ingredient, an effective amount of a non-human, mammalian monoclonal receptor that reacts with ganglioside $GD_2$ to form an immunocomplex and is produced and secreted by a hydridoma having the ATCC accession number HB 8568, said system also including indicating means that, when introduced into a sample, provides a means of detecting ganglioside $GD_2$ immunocoplexed with said receptor.

6. The diagnostic system of claim 5 wherein said indicating means is bonded to said monoclonal receptor.

7. The diagnostic system of claim 5 wherein said monoclonal receptor Fab fragment portions of antibodies individually bonded to said indicating means.

8. The diagnostic system of claim 5 wherein said monoclonal receptor includes antibodies individually bonded to said indicating means.

9. A composition for killing neuroblastoma tumor cells having ganglioside $GD_2$ expressed thereon comprising an effective amount of a non-human, mammalian monoclonal receptor produced and secreted by a hybridoma having the ATCC accession number HB 8568, complement and a physiologically tolerable diluent, said monoclonal receptor being capable of binding to said gangliside GD2 expressed on said tumor.

10. The composition of claim 9 wherein said monoclonal recpetor includes a cytotoxic drug bonded thereto, said cytotoxic drug further acting to kill tumor cells.

11. A method of killing neuroblastoma tumor cells that have ganglioside $GD_2$ expressed on cell surfaces comprising contacting said cells with a composition containing a physiologically tolerable diluent mixed with an effective amount of non-human, mammalian monoclonal antibodies that bind to ganglioside $GD_2$ and are produced and screted by a hybrdoma having the ATCC accession number HB 8568, said contacting being carried out in the presence of complement.

12. The method of claim 11 wherein said monclonal receptor includes a cytotoxic drug bonded thereto, said cytotoxic drug further acting to kill tumor cells.

13. A solid phase assay method for detecting the presence of ganglioside $GD_2$ in a sample to be assayed comprising the steps of:
   (a) providing a solid matrix on which to assay a sample;
   (b) admixing an aliquot of a liquid sample to be assayed for the presence of ganglioside $GD_2$ with said solid matrix to form a solid-liquid phase admixture;
   (c) maintaining said admixture for a predetermined time sufficient for ganglioside $GD_2$ present in the sampel to bind to said solid matrix and form a solid phase support;
   (d) separating the solid and liquid phases;
   (e) admixing a non-human, mammalian monoclonal receptor produced and screted by a hydridoma having the ATCC accession number HB 8568 with the separated solid phase to form a second solid-liquid phase admisture;
   (f) maintainaing said second solid-liquid phase admixture for a predetermined time sufficient for said receptor to immunocomplex with ganglioside $GD_2$ present in said sample;
   (g) separating the solid and liquid phases; and
   (h) detemining the presence of ganglioside $GD_2$ that immunocomplexed with said receptor.

14. The method of claim 13 further comprising the additional steps of:
  (i) admixing a liquid solution containing an indicator labelling means with the solid phase obtained after step (g) to form a third solid-liquid phase admixture, said indicator labelling means providing a means of detecting the presence of said receptor that reacted with ganglioside $GD_2$;
  (ii) maintaining said admixture for a predetermined time sufficient for said indicator labelling means to immunocomplex with said receptor;
  (iii) separating the solid and liquid phases of said third solid-liquid phase admixture; and
  (iv) determining the presence of receptor that immunocomplexed with ganglioside $GD_2$.

15. The method of claim 14 wherein said sample contains cells suspended in an aqueous medium, said cells affixing to said solid matrix.

16. The method of claim 14 wherein said sample contains serum or plasma.

17. An assay method for detecting the presence of ganglioside $GD_2$ in sample to be assayed comprising the steps of:
  (a) providing a sample to be assayed;
  (b) contacting said sample with a non-human, mammalian monoclonal receptor, said receptor being produced and secreted by a hybridoma having the ATCC accession number HB 8568 and said receptor binding to ganglioside $GD_2$;
  (c) maintaining said contact for a predetermined time sufficient for said receptor to react with ganglioside $GD_2$ present in said sample to form an immunocomplex;
  (d) contacting said immunocomplex with an indicator labelling means for a predetermined time sufficient for said indicator labelling means to immunocomplex with said receptor, said indicator labelling means providing a means of determining the p resence of receptor that reacted with ganglioside $GD_2$; and
  (e) determining the presence of receptor that reacted with ganglioside $GD_2$.

18. The method of claim 17 wherein said sample contains neuroectodermal tissues.

19. An assay method for detecting the presence of ganglioside $GD_2$ in a sample to be assayed comprising the steps of:
  (a) providing a sample to be assayed;
  (b) contacting said sample with a first non-human, mammalian monoclonal receptor produced and screted by a hybridoma having the ATCC accession number HB 8568, said first receptor binding to ganglioside $GD_2$;
  (c) maintaining said contact for a predetermined time sufficient for said first receptor to react with ganglioside $GD_2$ present in said sample to form an immunocomplex;
  (d) removing unreacted first receptor from said immunocomplex-containing sample;
  (e) admixing the immunocomplex formed with a secodn receptor that binds to said first receptor;
  (f) maintaining said asdmixture for a poredetermined time sufficient for said second recetor to react with said first receptor of the immunocomplex to form a second immunocomplex; and
  (g) determining the presence of second receptor that reacted with said first receptor immunocomplexed with ganglioside $GD_2$.

20. The method of claim 19 wherein said sample contains neuroectodermal tissues.

* * * * *

UNITED STATES PATENT AND TRADEMARK OFFICE
CERTIFICATE OF CORRECTION

PATENT NO. : 4,675,287

DATED : June 23, 1987

INVENTOR(S) : Ralph A. Reisfeld et al.

It is certified that error appears in the above-identified patent and that said Letters Patent is hereby corrected as shown below:

Column 7, line 33, "F(ab2" should read -- $F(ab')_2$ --.

Column 7, line 34, "F(ab2" should read -- $F(ab')_2$ --.

Columns 11 and 12, Table I, should appear as shown on the attached sheet

TABLE I

Reactivity of Mab 126 with Different Cell Lines in ELISA Assay

| Cell line | Tumor type | Reactivity | Cell line | Tumor type | Reactivity |
|---|---|---|---|---|---|
| Neuroblastomas | | | | | |
| LAN-1 | | +++[1] | LG2 | B-lymphoblastoid | - |
| LAN-2 | | +++ | L14 | cells | - |
| LAN-5 | | +++ | Molt-4 | T-cell leukemia | - |
| SK-N-SH | | +++ | HPB-All | acute lymphoblastoic leukemia | - |
| | | | Daudi | Burkitt Lymphoma | - |
| Melanomas | | | T 291 | Adeno Carcinoma (lung) | - |
| M14 | | +++ | CALU 6 | Anaplastic Carcinoma | - |
| M21 | | +++ | SCI-I185 | Squamous Carcinoma (skin) | - |
| FM3 | | +++ | UCLAP3 | Adeno Carcinoma (lung) | - |
| FM8 | | +++ | SW13 | Adeno Carcinoma (adrenal cortex) | ++[3] |
| FL2 | | +++ | | | |
| Foss | | +++ | Panc 1 | Pancreatic Carcinoma | - |
| Mueller | | +++ | H69 | Oat cell Carcinoma | ++ |
| Gliomas | | | WIL-TU-1 | Wilms Tumor | |
| U373 MG | | -[2] | SK-ES-2 | Ewing sarcoma | - |
| U138 MG | | +++ | U-20S | Osteogenic sarcoma | - |
| U87 MG | | +++ | A204 | Rhabdomyosarcoma | - |

1  "+++" indicates binding reactivity is more than four times higher than non-immune Ig from the myeloma partner, IgX63.

2  "-" indicates that no binding reactivity was observed.

3  "++" indicates binding reactivity is 3-4 times higher than IgX63.

UNITED STATES PATENT AND TRADEMARK OFFICE
CERTIFICATE OF CORRECTION

PATENT NO. : 4,675,287

DATED : June 23, 1987

INVENTOR(S) : Ralph A. Reisfeld et al.

It is certified that error appears in the above-identified patent and that said Letters Patent is hereby corrected as shown below:

Column 15, line 17, under M21, insert --1--

Column 28, line 9, delete "$H_2O_2$" and insert --$H_2SO_4$--

Claim 1, line 3, delete "the" and insert --with--

Claim 4, line 2, delete "receptr" and insert --receptor--

Claim 7, line 2, before "Fab" insert --includes--

Claim 13, line 12, delete "sampel" and insert --sample--

Claim 13, line 20, delete "maintainaing" and insert --maintaining--

Claim 19, line 7, delete "screted" and insert --secreted--

Claim 19, line 17, delete "codn" and insert --cond--

Claim 19, line 18, delete "poredetermined" and insert --predetermined--

UNITED STATES PATENT AND TRADEMARK OFFICE
CERTIFICATE OF CORRECTION

PATENT NO. : 4,675,287

DATED : June 23, 1987

INVENTOR(S) : Ralph A. Reisfeld et al.

It is certified that error appears in the above-identified patent and that said Letters Patent is hereby corrected as shown below:

Claim 19, line 19, delete "recetor" and insert -- receptor --.

Signed and Sealed this

Fifth Day of July, 1988

Attest:

DONALD J. QUIGG

*Attesting Officer*  *Commissioner of Patents and Trademarks*